US010646228B2

(12) United States Patent
Hayashi et al.

(10) Patent No.: US 10,646,228 B2
(45) Date of Patent: May 12, 2020

(54) ENDOSCOPIC CLIP DEVICE AND CLIP

(71) Applicant: SUMITOMO BAKELITE CO., LTD., Shinagawa-ku (JP)

(72) Inventors: Takuya Hayashi, Akita (JP); Masao Ikeda, Akita (JP); Hiroshi Utsugi, Akita (JP); Etsuro Yamabe, Akita (JP); Hideaki Matsunami, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 274 days.

(21) Appl. No.: 15/559,641

(22) PCT Filed: Aug. 21, 2015

(86) PCT No.: PCT/JP2015/073525
§ 371 (c)(1),
(2) Date: Sep. 19, 2017

(87) PCT Pub. No.: WO2016/157565
PCT Pub. Date: Oct. 6, 2016

(65) Prior Publication Data
US 2018/0333156 A1    Nov. 22, 2018

(30) Foreign Application Priority Data

Mar. 31, 2015   (JP) ................ 2015-073711
Mar. 31, 2015   (JP) ................ 2015-073712
Mar. 31, 2015   (JP) ................ 2015-073713

(51) Int. Cl.
A61B 17/122       (2006.01)
A61B 17/128       (2006.01)
(Continued)

(52) U.S. Cl.
CPC ........ A61B 17/122 (2013.01); A61B 1/00101 (2013.01); A61B 1/00112 (2013.01);
(Continued)

(58) Field of Classification Search
CPC ............. A61B 17/122; A61B 17/1222; A61B 17/1227; A61B 17/128; A61B 17/1285; A61B 2017/12004
See application file for complete search history.

(56) References Cited

U.S. PATENT DOCUMENTS

| 2002/0151916 A1 | 10/2002 | Muramatsu et al. |
| 2008/0033239 A1 | 2/2008 | Kogiso |
| 2013/0072945 A1 | 3/2013 | Terada |
| 2013/0072946 A1 | 3/2013 | Terada |

FOREIGN PATENT DOCUMENTS

| EP | 1 547 529 A1 | 6/2005 |
| JP | 2004-121485 A | 4/2004 |

(Continued)

OTHER PUBLICATIONS

International Search Report dated Nov. 24, 2015 in PCT/JP2015/073525 filed Aug. 21, 2015.

Primary Examiner — Robert A Lynch
(74) Attorney, Agent, or Firm — Oblon, McClelland, Maier & Neustadt, L.L.P.

(57) ABSTRACT

An endoscopic clip device including a clip, a treatment instrument body comprising a sheath, an operation wire, and a distal connection portion, a sleeve accommodated inside the sheath and accommodating the connection portion in distal portion of the wire such that portion of inner diameter of the sleeve is smaller than outer diameter of the locking portion when the connection portion is drawable from the accommodation portion. The sleeve has diameter enlargement portion on distal side of the sleeve and elastically self-openable, a diameter reduction step portion on proximal side of the enlargement portion, and a sleeve body positioned on the proximal side of the enlargement portion from the step portion and having radial rigidity higher than that of the enlargement portion, and the inner diameter of the sleeve (Continued)

body is smaller than the outer diameter of the locking portion when the connection portion is drawable from the accommodation portion.

24 Claims, 21 Drawing Sheets

(51) Int. Cl.
    *A61B 1/00*           (2006.01)
    *A61B 17/00*         (2006.01)

(52) U.S. Cl.
    CPC ...... *A61B 17/1222* (2013.01); *A61B 17/1227* (2013.01); *A61B 17/1285* (2013.01); *A61B 17/128* (2013.01); *A61B 2017/00477* (2013.01); *A61B 2017/00836* (2013.01); *A61B 2017/00862* (2013.01)

(56) References Cited

FOREIGN PATENT DOCUMENTS

| | | | |
|---|---|---|---|
| JP | 2007-275542 | A | 10/2007 |
| JP | 2007-283080 | A | 11/2007 |
| JP | 2008-36003 | A | 2/2008 |
| JP | 2008-100108 | A | 5/2008 |
| JP | 2009-11784 | A | 1/2009 |
| JP | 2009-066226 | A | 4/2009 |
| JP | 2011-078592 | A | 4/2011 |
| JP | 2013-63108 | A | 4/2013 |
| JP | 2013-63109 | A | 4/2013 |

ENDOSCOPIC CLIP DEVICE AND CLIP

TECHNICAL FIELD

The present invention relates to an endoscopic clip device, a clip, and an endoscopic treatment instrument.

Priority is claimed on Japanese Patent Application No. 2015-073711, filed on Mar. 31, 2015, Japanese Patent Application No. 2015-073712, filed on Mar. 31, 2015, and Japanese Patent Application No. 2015-073713, filed on Mar. 31, 2015, the entire content of which is incorporated herein by reference.

BACKGROUND ART

There is provided a clip device which excises a living body tissue in a body lumen by using an endoscope, and which ligates an excised site and performs hemostasis thereon. With regard to this type of endoscopic clip device and a medical clip used for the device (hereinafter, abbreviated as a clip), Patent Document 1 discloses a technique in which a distal end arrowhead hook of an operation wire disposed in a treatment instrument body is inserted into and connected to a connection member in a proximal portion of the clip. If the operation wire is drawn in a state where the arrowhead hook is inserted into the connection member, the living body tissue is ligated. If the operation wire is further strongly drawn in this state, a small diameter portion of the connection member is broken. Then, in a state where the living body tissue is ligated, the clip is caused to indwell the inside of the body lumen. The connection member has a pair of semi-cylindrical passage holes facing each other. These passage holes are spread, thereby causing the arrowhead hook to be pushed into and connected to the connection member.

The clip has a pair of arms facing each other, and the arms are closed so that distal ends of the arms move close to each other. The arms have a self-openable force. The arms are closed against this power, and are accommodated in a sheath. In this state, the arms are inserted into a forceps hole of an endoscope. If the arms reach the vicinity of the living body tissue, the arms are caused to protrude from the sheath, and are opened using an elastic restoration force. Thereafter, the operation wire is drawn, and the clip is pulled into the sheath again, thereby closing the arms. In this manner, the living body tissue can be gripped and ligated by the arms.

Here, when the living body tissue is ligated, an orientation in which the arms of the clip are closed needs to align with the living body tissue to a desired degree. Therefore, the operation wire is rotated to generate torques, thereby transmitting the torques to the clip via the arrowhead hook and the connection member. According to the device disclosed in PTL 1, if an operation unit body is rotated to generate the torques, the operation wire and the arrowhead hook are rotated in conjunction with the operation unit body. Furthermore, the connection member is rotated due to a frictional force generated between the arrowhead hook and the connection member. In this manner, a pushing tube and the clip are rotated to generate the torques, thereby enabling the orientation of the arms to be adjusted.

In addition, as an endoscope technique has been developed in recent years, in many cases, medical treatments have been increasingly performed, such as observation inside the body lumen by using the endoscope and excision of the living body tissue by using the endoscope. As a result, there are increasing demands for an endoscopic treatment instrument which can ligate the living body tissue and perform the hemostasis thereon after treatment. As a treatment technique using the endoscope is improved, it is expected that the treatment such as the hemostasis using the endoscopic treatment instrument is reliably completed in a limited space inside the body lumen.

As the clip used for this type of endoscopic treatment instrument, PTL 1 and PTL 2 respectively disclose examples as follows.

PTL 1 discloses a clip unit used for the above-described purpose. The clip mounted on the clip unit has a shape in which a plurality of arms intersect each other once on a proximal side. Since the clip has this shape, when the clip is pulled into the clip unit in a state where the clip protrudes outward from the clip unit (state illustrated in FIG. 3 in PTL 1), the clip is opened once (state illustrated in FIGS. 4, 5A, and 5B in PTL 1), and thereafter, the clip is closed (state illustrated in FIG. 6 in PTL 1).

PTL 2 discloses a clip device used for the above-described purpose. The disclosed clip mounted on the clip device has both a shape in which the plurality of arms intersect each other once on the proximal side, similarly to PTL 1 (FIG. 12 in PTL 2), and a shape in which the plurality of arms are terminated on the proximal side without intersecting each other (FIG. 1 in PTL 2).

CITATION LIST

Patent Literature

[PTL 1] Japanese Unexamined Patent Application, First Publication No. 2004-121485

[PTL 2] Japanese Unexamined Patent Application, First Publication No. 2008-100108

SUMMARY OF INVENTION

Technical Problem

However, according to the endoscopic clip device disclosed in PTL 1, the broken connection member needs to be discarded after being collected and removed from the arrowhead hook. Consequently, the procedure is complicated, thereby causing a possibility that an infection problem may arise.

On the other hand, the hemostasis is generally performed on the excised site of the living body tissue by using multiple clips. Therefore, in the hemostasis, a series of procedures needs to be quickly performed as follows. The operation wire is connected to the clip. The operation wire is inserted into the body lumen through the endoscope. The living body tissue is ligated, and the clip is caused to indwell the body lumen. Furthermore, the operation wire is pulled outward from the body, and the next clip is connected thereto again. In order to save a time required for exchanging the treatment instrument body when the multiple clips are used in the ligation and indwelling operation, the treatment instrument body needs durability enough to be used repeatedly many times.

In addition, due to the following two reasons, the device disclosed in PTL 1 has a problem in that even if the operation unit body is rotated to generate the torques, the arm of the clip cannot always be oriented in a desired direction. The first reason is that the arrowhead hook is frictionally rotated inside the semi-cylindrical passage hole. Accordingly, even if the operation unit body or the operation wire is rotated to generate the torques, only some of the torques are transmitted to the connection member. Therefore, even if a user wishes to rotate the arm of the clip by a desired angle, the user cannot accurately know how large torque angle has to be provided for the operation unit body. The second reason is that the arrowhead hook or the connection member receives the frictional force by coming into contact with an inner surface of the sheath. Accordingly, while some of the torques applied to the connection member from the arrowhead hook are further lost, the torques are transmitted to the clip. For this reason, even if the operation unit body or the operation wire is rotated to generate the torques, the rotation force is not substantially transmitted to the arm of the clip, or there is a considerable delay until the arm of the clip is rotated after the operation unit body is rotated to generate the torques. Consequently, it becomes difficult to direct the arm of the clip in the desired orientation.

Here, in a case of using the clip having a shape in which the plurality of arms intersect each other once on the proximal side, due to the shape in which the arms intersect each other on the proximal side, a ratio of the size of the proximal portion of the clip increases relative to the size of the entire clip. Therefore, there are restrictions since it is necessary to sufficiently provide an internal space of the clip unit which accommodates the clip. In some cases, there is a problem from the viewpoint of miniaturization.

In addition, in a case of using the clip having a shape in which the plurality of arms are terminated on the proximal side without intersecting each other, the miniaturization is likely to be achieved compared to the case of using the clip having the shape described in the previous paragraph. However, there is a difficulty in that the arms are less likely to be widely opened. In addition, when the clip is clamped, the arms are steeply closed. Consequently, when the clip fails to grip a target living body tissue, the procedure is less likely to be performed again after the clip is opened again. In some cases, there is a problem from the viewpoint of handling.

The present invention is made in view of the above-described problems, and an object thereof is to provide an endoscopic clip device and a clip in which a connection operation between the clip and an operation wire is facilitated, and in which a procedure can be quickly performed by reducing an exchange frequency of a treatment instrument body. In addition, the present invention aims to provide the endoscopic clip device which can accurately direct an arm of the clip in a desired orientation. Furthermore, the present invention aims to provide the clip which is not only widely openable but also likely to be accurately handled, and an endoscopic treatment instrument on which the clip is mounted.

Solution to Problem

According to an aspect of the present invention, there is provided an endoscopic clip device including a clip that comprises a plurality of arms for gripping a living body tissue and a locking portion disposed on a proximal side of the arms, and a treatment instrument body that comprises an elongated sheath, and an operation wire which is inserted into the sheath so as to be movable forward and backward, and in which a chunky distal connection portion is disposed in a distal end. The locking portion of the clip comprises an accommodation portion which internally has a space for accommodating the distal connection portion, and a protruding portion which is formed to protrude inward on a proximal side of the accommodation portion. The distal connection portion is pushed against the protruding portion from the proximal side so that the protruding portion is elastically deformed outward, the accommodation portion is opened so that the distal connection portion can be accommodated in a forward/backward movement direction of the operation wire, and the distal connection portion passes through the protruding portion on a distal side in the forward/backward movement direction so that the protruding portion is elastically restored inward. In a state where the distal connection portion is accommodated in the accommodation portion, the distal connection portion draws the operation wire to the proximal side in the forward/backward movement direction so that the arms are closed to grip the living body tissue, the distal connection portion further draws the operation wire to the proximal side so that the distal connection portion causes the protruding portion to be deformed outward and the accommodation portion is opened, and the distal connection portion is drawable from the accommodation portion.

In addition, according to an aspect of the present invention, there is provided a clip used for the endoscopic clip device. The clip includes a plurality of arms for gripping a living body tissue, and a locking portion that is disposed on a proximal side of the arms. The locking portion comprises a base which is connected to the proximal side of the arms, an accommodation portion which is configured to comprise a plurality of projection pieces formed to project to the proximal side from the base and which internally has a space, and protruding portions respectively formed to protrude inward in a distal portion on the proximal side of the projection pieces.

In addition, according to an aspect of the present invention, there is provided an endoscopic clip device including a clip that comprises a plurality of arms for gripping a living body tissue, and a locking portion disposed on a proximal side of the arms, and a treatment instrument body that comprises an elongated sheath, and an operation wire which is inserted into the sheath so as to be movable forward and backward, and in which a distal connection portion is disposed in a distal end. The locking portion and the distal connection portion are locked and connected to each other around an axis of the operation wire. A cylindrical sleeve which accommodates the distal connection portion is disposed in the distal portion of the operation wire. The operation wire is rotated to generate torques so that the locking portion, the distal connection portion, and the sleeve are axially rotated around the axis inside the sheath.

In addition, according to an aspect of the present invention, there is provided a clip used for an endoscopic treatment instrument comprising an elongated sheath and an operation wire inserted into the sheath so as to be movable forward and backward. The clip includes a locking portion that engages with a distal side of the operation wire, a plurality of arms that are disposed on the distal side from the locking portion, and that are opened outward using a self-openable force, a clamping member into which the plurality of arms are inserted, and whose position relative to the plurality of arms is displaced from the proximal side to the distal side so that the plurality of arms are closed inward, and a plurality of claws that are disposed on the distal side from the plurality of arms, and that protrude inward. Each of the arms comprises a bending portion which is bent outward so that a curvature radius on the proximal side is larger than a curvature radius on the distal side.

According to the aspect of the present invention, a portion (bending portion) of the arms is bent outward. Accordingly, the arms are widely openable.

In addition, when the clamping member is displaced from the proximal side to the distal side and the bending portions are closed, the arms are gently closed with respect to the displacement while the clamping member is located on the proximal side of the bending portion. Accordingly, the clamping member can seek for the living body tissue serving as a ligation target, while moving forward and backward, thereby further facilitating accurate handling. Therefore, the operability of the procedure performed by the endoscopic treatment instrument using this clip is improved.

Advantageous Effects of Invention

According to the endoscopic clip device and the clip of the present invention, the chunky distal connection portion of the distal end of the operation wire is pushed against the protruding portion of the clip from the proximal side so that the accommodation portion is opened and the distal connection portion is connectable thereto. Reversely, in a state where the distal connection portion is accommodated in the accommodation portion, the protruding portion is deformed by drawing the operation wire, the accommodation portion is opened again, and the distal connection portion is drawable. Therefore, the forward/backward operation of the operation wire can facilitate the attachment/detachment operation between the distal connection portion and the clip. In addition, the distal connection portion has a chunky shape, and the locking portion of the clip is entirely deformed so as to perform the attachment/detachment operation. Accordingly, the distal connection portion is restrained from being worn, thereby providing the treatment instrument body with excellent durability. Therefore, a procedure can be quickly performed since the exchange frequency of the treatment instrument body can be reduced.

In addition, according to the endoscopic clip device of the present invention, the locking portion of the clip and the distal connection portion of the operation wire are locked and connected to each other around the axis of the operation wire. Accordingly, the torque applied to the operation wire is satisfactorily transmitted to the clip. Moreover, the cylindrical sleeve is axially rotated inside the sheath in a state where the sleeve accommodates the locking portion of the clip and the distal connection portion of the operation wire, thereby preventing the locking portion or the distal connection portion from receiving the frictional force by being brought into contact with the inner surface of the sheath. In this manner, according to the present invention, the arm of the clip is accurately directed in a desired direction.

Furthermore, according to the present invention, there is provided the clip which is not only widely openable but also likely to be accurately handled, and the endoscopic treatment instrument on which the clip is mounted.

DESCRIPTION OF EMBODIMENTS

Figure 1:
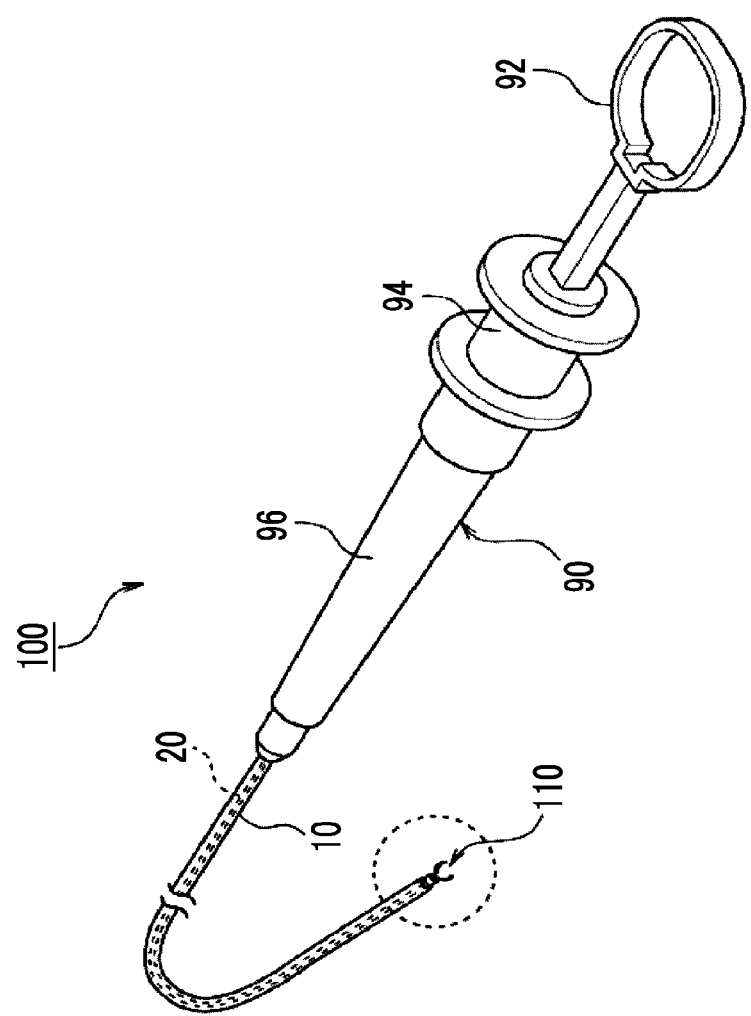
FIG. 1 is a perspective view illustrating an example of an endoscopic clip device according to a first embodiment and a second embodiment of the present invention.

Hereinafter, embodiments according to the present invention will be described with reference to the drawings. In each drawing, the common reference numerals will be given to the corresponding configuration elements, and repeated description will be appropriately omitted. First, a first aspect according to the present invention will be mainly described.

Figure 2:
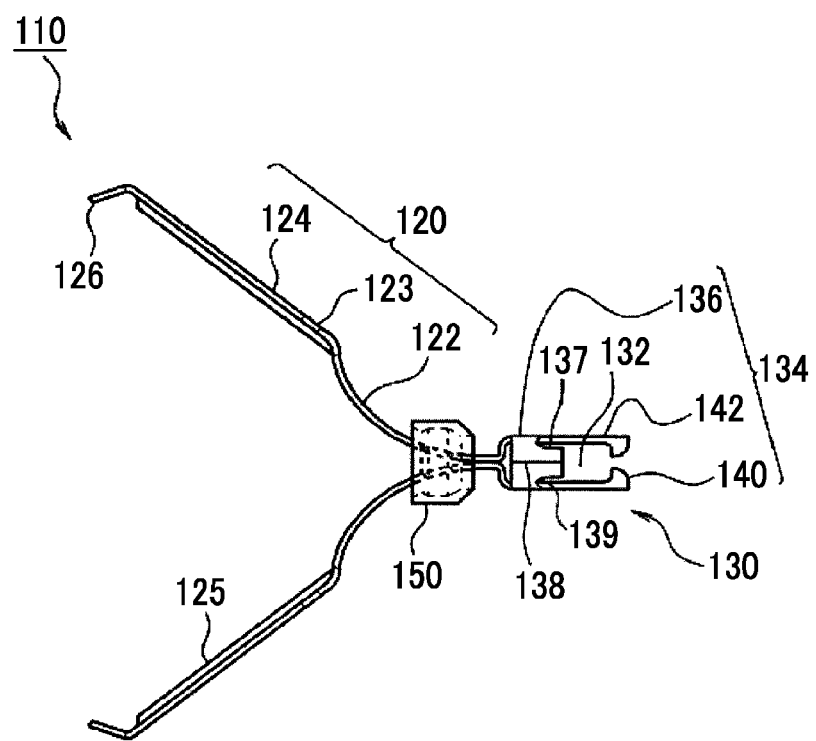
FIG. 2 is a side view of a clip.
Figure 3A:
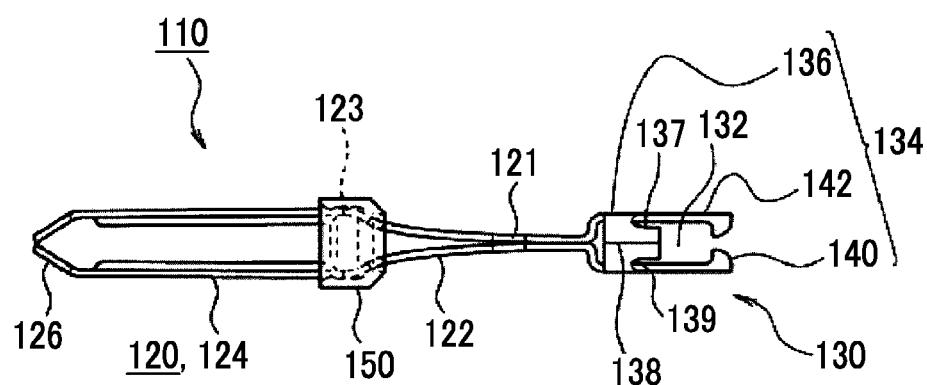
FIG. 3A is a side view illustrating the clip in a closed state.
Figure 3B:
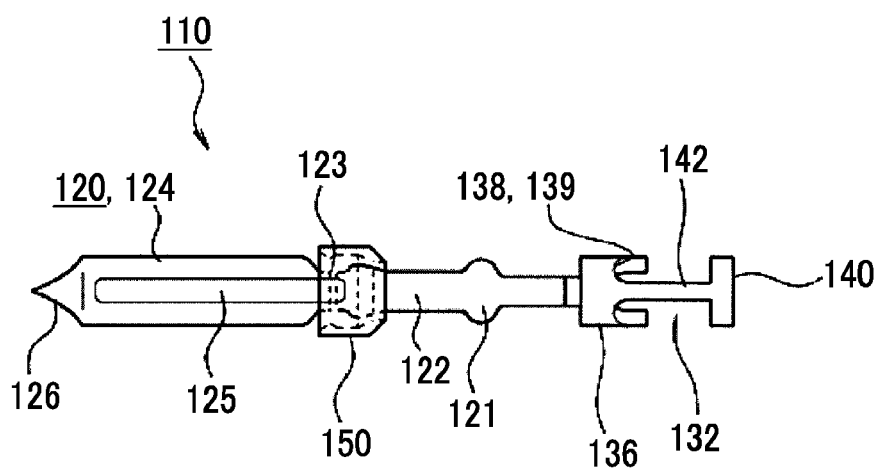
FIG. 3B is a plan view of FIG. 3A.
Figure 4:
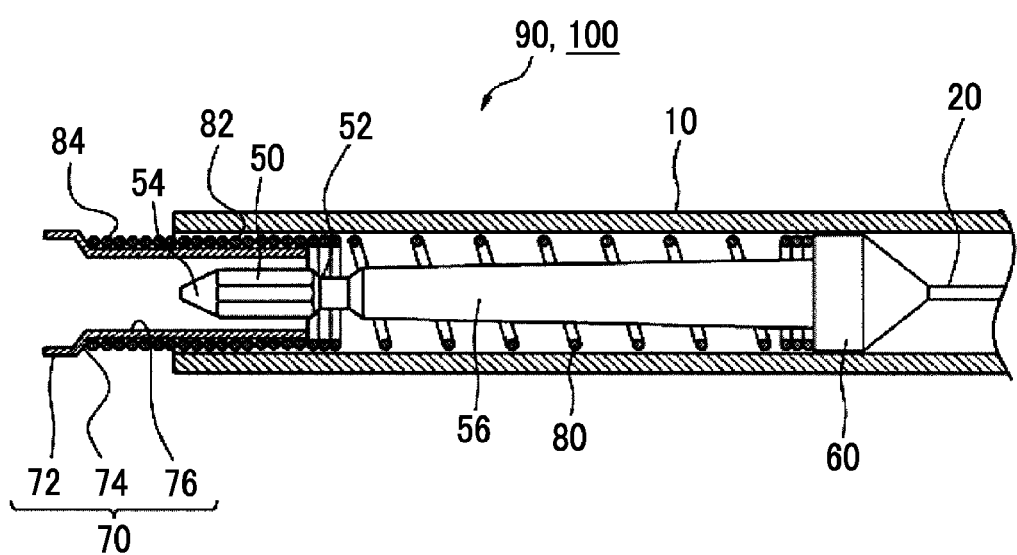
FIG. 4 is a view for describing a distal portion of a treatment instrument body.

FIG. 1 is a perspective view illustrating an example of an endoscopic clip device (hereinafter, abbreviated as a clip device in some cases) 100 according to embodiments of first and second aspects of the present invention. FIG. 2 is a side view of the clip 110. FIG. 3A is a side view illustrating a clip 110 in a closed state, and FIG. 3B is a plan view thereof. FIG. 4 is a view for describing a distal portion of a treatment instrument body 90, and is a schematic longitudinal sectional view of the treatment instrument body 90 which is taken along an axial direction.

In the present specification, unless otherwise specified, the "axial direction" means a forward/backward movement direction of an operation wire 20. In addition, unless otherwise specified, a "cross section" means a longitudinal cross section in which the endoscopic clip device 100 is cut in the axial direction.

In FIG. 4, for the sake of convenience, a sheath 10, a diameter reduction sleeve 70, and an elastic portion 80 are hatched in a cross section, and the operation wire 20, a distal connection portion 50, a strut 56, and a centering portion 60 are illustrated using a side view. The description subsequent to FIGS. 5A and 5B will be the same as above. In FIGS. 6 to 9A and 9B, only an end surface of the elastic portion 80 is illustrated, and winding wires appearing behind each drawing are omitted.

The clip device 100 is used after being inserted into a forceps hole (not illustrated) of an endoscope. Specifically, the sheath 10 of the clip device 100 is inserted into the forceps hole of the endoscope indwelling a body lumen from a proximal side, a distal end of the sheath 10 is protruded from a distal opening of the forceps hole, and the clip 110 is further exposed from the sheath 10, thereby ligating a living body tissue. The clip 110 can be used in this way. The living body tissue to be ligated can include a body tube such as a blood vessel, in addition to a mucosal wall such as a treatment target site of endoscopic submucosal dissection (ESD).

Unless otherwise specified, the "distal side" is referred to as a side far away from an operator of the endoscopic clip device 100 in the endoscopic clip device 100 or the clip 110 mounted thereof, and specifically means a side having an arm 120 of the clip 110. In addition unless otherwise specified, the "proximal side" means a side close to the operator in the endoscopic clip device 100 or the clip 110.

In addition, a configuration element of the endoscopic clip device 100 which moves to the distal side is referred to as forward movement, and reverse movement to the proximal side is referred to as backward movement in some cases.

The endoscopic clip device 100 includes the clip 110 and the treatment instrument body 90. As respectively illustrated in FIGS. 2 and 3, the clip 110 has a plurality of arms 120 for gripping a living body tissue, and a locking portion 130 disposed on the proximal side of the arms 120. On the other hand, as illustrated in FIG. 4, the treatment instrument body 90 has the elongate sheath 10 and an operation wire 20 which is inserted in the sheath 10 so as to be movable forward and backward, and whose distal end has a chunky distal connection portion 50.

Here, the description that the distal connection portion 50 has a "chunky shape" means that the distal connection portion 50 is thicker than the locking portion 130, that the distal connection portion 50 is connected to the locking portion 130, and that the displacement of the distal connection portion 50 is sufficiently smaller than the displacement of the locking portion 130 when the distal connection portion 50 is removed from the locking portion 130. A specific shape of the chunky distal connection portion 50 is not particularly limited. As illustrated in FIG. 4, the shape may be a shell shape whose diameter decreases toward the distal side, and may be a columnar shape or a spherical shape.

A specific structure of the treatment instrument body 90 included in the clip device 100 is not particularly limited. FIG. 1 illustrates an example of the treatment instrument body 90 including a finger ring 92, a slider 94, and a main body shaft 96. A user of the clip device 100 inserts a finger (for example, a thumb) into the finger ring 92. In a state where the user pinches the slider 94 with other fingers (for example, an index finger and a middle finger), the user performs an operation by relatively moving the slider 94 to the main body shaft 96. In this manner, the operation wire 20 connected to the slider 94 is moved forward and backward inside the sheath 10. In addition, the treatment instrument body 90 is entirely rotated about the axis, thereby rotating the operation wire 20 together with the slider 94. In a case where the sheath 10 is in close contact with a wall surface of the forceps hole of the endoscope, the operation wire 20 is axially rotated inside the sheath 10. Hereinafter, the description that the treatment instrument body 90, the operation wire 20, and the clip 110 are axially rotated is referred to as "torque rotation" in some cases.

The clip 110 ligates the living body tissue, and can perform treatment, for example, such as hemostasis, colporrhaphy, and marking by ligating the living body tissue with the arms 120. The arms 120 have a self-openable force, and the arms 120 in a closed state are protruded from the sheath 10 as described later. In this manner, the arms 120 are naturally opened and brought into an opened state. Here, "self-opening" means an attempt to open itself by repelling against an external closing force.

The arms 120 and the locking portion 130 are integrally formed of a single material. More specifically, a metal plate material is punched out, pushed and bent so as to prepare the arms 120 and the locking portion 130. The metal material can include stainless steel, titanium, or a titanium alloy, but the metal material is not limited thereto. In addition, the above-described metal material may be subjected to corrosion-resistant coating treatment.

The pair of facing arms 120 of the clip 110 according to the present embodiment respectively include a proximal portion 122 protruding from the locking portion 130 toward the distal side (the left side in FIG. 2), and an arm body 124 continuous with the proximal portion 122 on the distal side. The proximal portion 122 is bent outward toward the distal side.

Here, the description "outward" means a direction away from an axis of the operation wire 20 or an extension line of the axis. For example, the description represents an outward direction in a radial direction. The description "inward" means a direction close to the axis of the operation wire 20 or the extension line of the axis. For example, the description represents an inward direction in the radial direction.

The arm body 124 is linearly formed, and the distal end of the arm body 124 has a claw 126. The arm body 124 and the claw 126 are gripping regions for mainly gripping the living body tissue. The claw 126 protrudes inward from the pair of arm bodies 124, and digs into the living body tissue, thereby improving a gripping force of the clip 110. The arms 120 are bent at a boundary between the proximal portion 122 and the arm body 124. At the boundary, a narrow width portion 123 is formed in which a width dimension of the arms 120 is locally reduced.

The clip 110 (however, the clamping member 150 is excluded) according to the present embodiment is made of a single material. That is, one claw 126, one arm body 124, and one proximal portion 122, and the other claw 126, the other arm body 124, and the other proximal portion 122 are seamlessly and continuously formed via the locking portion 130.

A reinforcement portion 125 is formed in the arm body 124 by pushing (embossing) a portion of the center in the width direction. Since the reinforcement portion 125 is formed, the thickness dimension of the arm body 124 increases, and bending rigidity of the arm body 124 is improved. In this manner, a strong gripping force for the living body tissue can be obtained. In the clip 110 according to the present embodiment, the reinforcement portion 125 is continuously formed in the arm body 124 from the distal portion excluding the claw 126 to the proximal portion leading to the narrow width portion 123.

The clip 110 further includes an annular clamping member 150 mounted on an outer periphery of the plurality of arms 120. The clamping member 150 is mounted so as to be movable forward to and backward from the arm 120. The clamping member 150 is moved to the distal side relative to the arm 120. In this manner, the arm 120 in an opened state (refer to FIG. 2) can be clamped by the clamping member 150 against the self-openable force. This brings the arm 120 into a closed state (refer to each drawing in FIG. 3). In addition, the clamping member 150 is moved backward relative to the arm 120, thereby opening the arm 120 using the self-openable force. The annular clamping member 150 may have an entirely annular shape whose entire circumferential surface is continuous in the circumferential direction, or may have a partially annular shape in which a notch or a slit is partially disposed in the circumferential direction.

The arm body 124 of the arm 120 is formed to be thicker than the proximal portion 122 or the narrow width portion 123, thereby prohibiting the clamping member 150 from moving forward to the arm body 124 over the narrow width portion 123. In addition, the proximal portion 122 has a widened portion 121 which is partially formed to be thick. An inner diameter of the proximal side of the clamping member 150 is smaller than the width dimension of the widened portion 121. That is, the clamping member 150 is prohibited from moving to the proximal side of the clip 110 over the widened portion 121. The clamping member 150 moves forward to and backward from the arm 120 in a length region between the widened portion 121 and the arm body 124. Then, the clamping member 150 is fitted to the narrow width portion 123. In this manner, the clamping member 150 is locked to the arm 120, thereby locking the clip 110 in a closed state.

As illustrated in FIGS. 2 and 3, the locking portion 130 of the clip 110 has an accommodation portion 134 internally having a space 132 for accommodating the distal connection portion 50, and a protruding portion 140 protruding inward on the proximal side of the accommodation portion 134. The distal connection portion 50 is accommodated in the space 132, thereby connecting the clip 110 and the operation wire 20 to each other.

The protruding portion 140 is a claw which is elastically deformed and opened so as to be spread out by the distal connection portion 50, and which is elastically restored so as to engage with and hold the distal connection portion 50.

The protruding portion 140 is disposed on the proximal side of the accommodation portion 134, and closes the space 132 so as to be partially or entirely openable. A shape, position, and size of the protruding portion 140 are not particularly limited. For example, the accommodation portion 134 may be annularly formed, and the protruding portion 140 may be formed to protrude inward in the radial direction from the circumferential surface of the annular accommodation portion 134. Alternatively, the accommodation portion 134 may be configured to comprise an annular base 136 and a projection piece 142 protruding from the base 136 to the proximal side, and the protruding portion 140 may be formed in the distal end of the projection piece 142.

The locking portion 130 includes the base 136 connected to the proximal end of the arm 120, and a plurality of projection pieces 142 projecting from the base 136 to the proximal side so as to form the accommodation portion 134. The protruding portions 140 are respectively formed in the distal portions on the proximal sides of the projection pieces 142.

The distal connection portion 50 of the operation wire 20 is accommodated in the space 132 surrounded by the base 136, the projection piece 142, and the protruding portion 140. The inner diameter of the base 136 is smaller than the maximum outer diameter of the distal connection portion 50, and the base 136 regulates forward movement of the distal connection portion 50. The protruding portion 140 regulates backward movement of the distal connection portion 50 accommodated in the space 132. The distal connection portion 50 accommodated in the space 132 may be constrained in a direction to the proximal end by the base 136 and the protruding portion 140, and may be prohibited from moving forward and backward inside the space 132. Alternatively, the distal connection portion 50 may be slightly movable forward and backward in the axial direction inside the space 132.

The projection piece 142 according to the present embodiment has a plate shape having a narrower width than the diameter of the distal connection portion 50. A sectional shape of the distal connection portion 50 is a polygonal shape, and preferably has a regular polygonal cross section. The distal connection portion 50 according to the present embodiment has a regular hexagonal cross section. That is, the distal connection portion 50 has six outer peripheral surfaces. The plurality of projection pieces 142 facing each other are arranged in the locking portion 130. The number of the projection pieces 142 is not limited, but it is preferable that the number is smaller than the number of the outer circumferential surfaces of the distal connection portion 50 having the polygonal cross section. Specifically, the locking portion 130 according to the present embodiment has two projection pieces 142.

The two projection pieces 142 are disposed at positions where the projection pieces 142 can respectively face the outer circumferential surface of the distal connection portion 50. More specifically, the two projection pieces 142 are disposed at positions which face each other at 180 degrees in the base 136 of the locking portion 130. Instead of the present embodiment, the three projection pieces 142 may be equally arranged to face each other at an interval of 120 degrees. A distance between the projection pieces 142 facing each other is set to a dimension which enables the projection pieces 142 to come into close contact with or to move close to the outer peripheral surface of the distal connection portion 50.

If the distal connection portion 50 is connected to the clip 110, the plurality of the projection pieces 142 come into close contact with or move close to the distal connection portion 50 so as to surround an outer peripheral surface 58 of the distal connection portion 50 accommodated in the accommodation portion 134. In this manner, if the distal connection portion 50 is rotated to generate torques, the outer peripheral surface of the distal connection portion 50 rotates the projection piece 142 about the axis, and the torques are applied to the clip 110 through the locking portion 130.

The protruding portion 140 formed in the distal end on the proximal side of the projection piece 142 is disposed on the circumference which is concentric with the base 136, and is formed in a partially arc shape. The individual protruding portion 140 has a partially arc shape whose central angle is approximately 120 degrees, and is formed so that the two protruding portions 140 can hold a region of approximately two thirds of the above-described circumference.

The base 136 has an annular shape formed by bending a plate material such as a metal material so that edges 138 abut on each other. The plurality of projection pieces 142 are arranged apart from each around the circular base 136. As illustrated in FIGS. 2 and 3A, a joint of the abutted edges 138 is located at an intermediate position between the projection pieces 142 adjacent to each other.

Figure 9A:
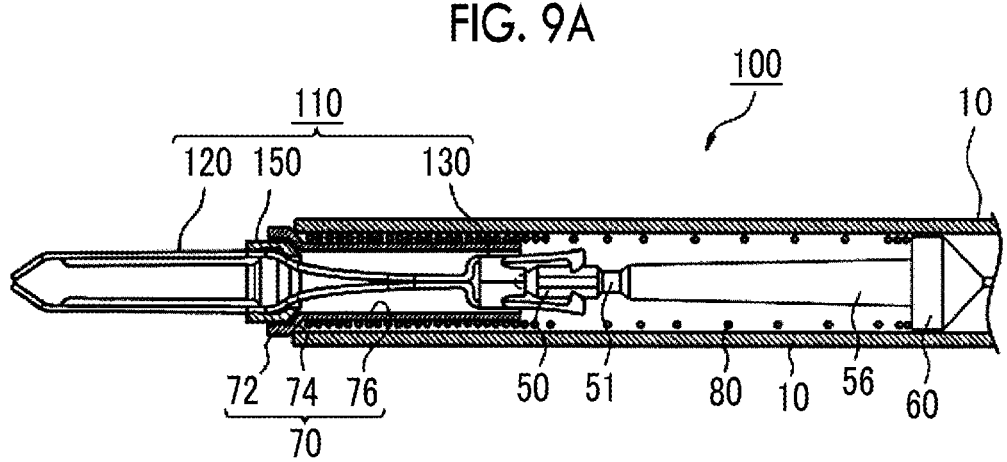
FIG. 9A is a view for describing a state where the distal connection portion is drawn out from the locking portion of the clip.
Figure 9B:
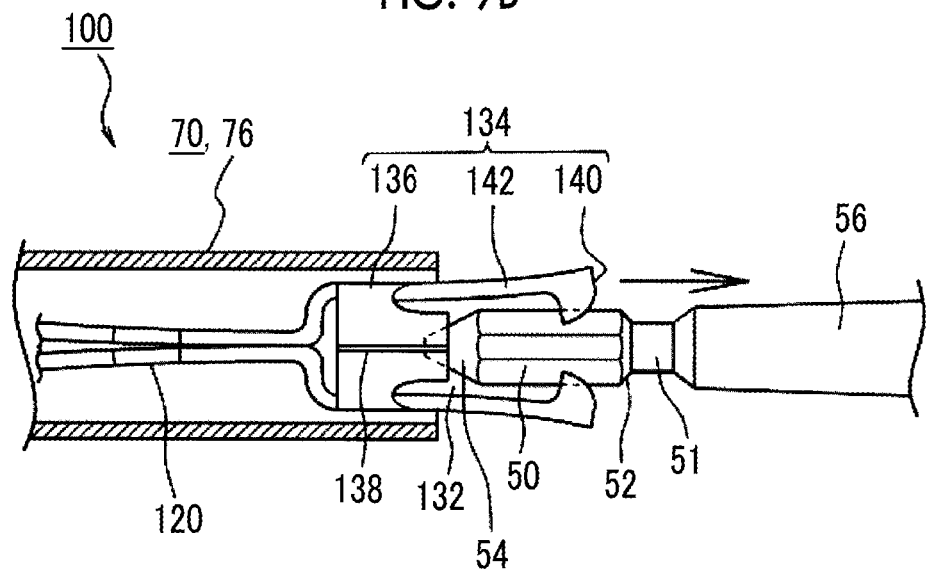
FIG. 9B is an enlarged view of FIG. 9A relating to the vicinity of the distal connection portion.

In this manner, as will be described with reference to FIGS. 5B and 9B, bending stress transmitted from the protruding portion 140 to the projection piece 142 when the distal connection portion 50 is inserted into the accommodation portion 134 or when the distal connection portion 50 is removed from the accommodation portion 134 is delivered to the annular base 136 as a deforming force in a direction in which the joint of the edges 138 is released. Therefore, the bending stress is consumed as an elastic force for enlarging the base 136, thereby restraining the projection piece 142 from being plastically deformed.

A specific shape of the annular base 136 is not particularly limited, and can include an example such as a cylindrical shape, a prismatic shape, or a combination thereof. In addition, the base 136 may have an entirely annular shape in which the joints of the edges 138 are in contact with each other, or may have a partially annular shape in which joints of the edges 138 are separated at a predetermined interval.

As illustrated in FIG. 3B, a plurality of the recesses 137 recessed toward the distal side are formed in the peripheral edge on the proximal side of the base 136. The projection piece 142 is formed to project from a bottom 139 of the recess 137 to the proximal side. In this manner, the projection piece 142 can be formed long while the dimension of the locking portion 130 is restrained in the axial direction.

When the distal connection portion 50 of the operation wire 20 is fitted to or removed from the accommodation portion 134, the projection piece 142 can be flexibly deformed.

A root portion on the distal side of the projection piece 142 is formed to be gradually thicker toward the bottom 139 of the recess 137, and is smoothly connected to the bottom 139. In this manner, the distal connection portion 50 of the operation wire 20 biases the protruding portion 140. In a case where the bending stress is applied to the projection piece 142, stress concentration on the root portion of the projection piece 142 is relieved, thereby restraining the projection piece 142 from being plastically deformed.

More specifically, the joint of the edges 138 in the locking portion 130 is disposed at a position having no recess 137 in the base 136. In this manner, the length of the joint of the edges 138 can be used as the total length in the axial direction of the base 136. Therefore, when the clip 110 is prepared by bending a plate material such as a metal material, the annular base 136 can be accurately formed into a desired shape.

The sheath 10 illustrated in FIG. 4 is a long and flexible tubular member. The sheath 10 is longer than the forceps hole of the endoscope used together with the clip device 100. For example, the sheath 10 can be configured to comprise a coil layer (not illustrated) around which a metal wire is wound long. An inner layer (not illustrated) made of fluorine-based polymer may be disposed on the inner peripheral surface of the coil layer. In addition, the sheath 10 may include a coil layer around which a resin wire is wound, or a flexible resin tube.

The inner diameter dimension of the sheath 10 has a size which slidably accommodates the centering portion 60 (to be described later) disposed in the distal end of the operation wire 20. In the sheath 10 according to the present embodiment, the clip 110 in a closed state can be accommodated inside the sheath 10 (refer to FIG. 6A). Specifically, the inner diameter of the sheath 10 is 100 µm to 2,400 µm, for example. In addition, the thickness dimension of the sheath 10 is 100 µm to 350 µm, for example. In this manner, the flexibility of the sheath 10 can be improved.

The operation wire 20 is inserted into the sheath 10 so as to be movable forward and backward in the axial direction. For example, the operation wire 20 is formed of a highly rigid metal material such as stainless steel, a corrosion-resistant coated steel wire, titanium, or a titanium alloy. The metal material configuring the metal plate can include stainless steel, titanium, or a titanium alloy. However, the metal material is not limited thereto. In addition, the above-described metal member may be appropriately subjected to corrosion-resistant coating treatment.

The distal end of the operation wire 20 has the centering portion 60, the strut 56, the distal connection portion 50, the elastic portion 80, and the diameter reduction sleeve 70. The centering portion 60 has a chunky shape whose diameter is larger than that of the operation wire 20, and is fixed to the distal end of the operation wire 20. The centering portion 60 includes a cylinder-shaped portion (cylindrical portion), and the outer diameter of the cylindrical portion is formed to be equal to or slightly smaller than the inner diameter of the sheath 10. As the operation wire 20 moves forward and backward inside the sheath 10, the centering portion 60 moves forward and backward while sliding inside the sheath 10. In this case, since the outer diameter of the centering portion 60 is substantially the same as the inner diameter of the sheath 10, the operation wire 20 moves forward and backward while being positioned in the vicinity of the axis of the sheath 10. Even in a case where the sheath 10 is inserted into the forceps hole of the bent endoscope (not illustrated), since the operation wire 20 is positioned on substantially the center line of the forceps hole, the path length of the operation wire 20 is not changed, thereby restraining the distal connection portion 50 or the clip 110 from unexpectedly protruding from the sheath 10.

The strut 56 is formed on the distal side of the operation wire 20 so as to protrude coaxially with the operation wire 20. The chunky distal connection portion 50 is integrally formed in the distal end of the strut 56. A neck portion 51 is formed between the strut 56 and the distal connection portion 50 (refer to FIG. 5B). The elastic portion 80 is disposed around the strut 56 so as to accommodate the strut 56. In a natural state illustrated in FIG. 4, the distal connection portion 50 is located inside the diameter reduction sleeve 70.

The distal portion of the distal connection portion 50 has a second inclined surface 54. The normal direction of the second inclined surface 54 is a direction which is oriented obliquely outward toward the distal side (leftward in FIG. 4). In this manner, as will be described later with reference to each drawing in FIG. 5, the distal connection portion 50 is pushed against the protruding portion 140 from the proximal side. In this manner, the second inclined surface 54 causes the protruding portion 140 to be elastically deformed outward.

In addition, a first inclined surface 52 is disposed in the proximal portion of the distal connection portion 50. The normal direction of the first inclined surface 52 is a direction which is oriented obliquely outward toward the proximal side. In this manner, as will be described later with reference to each drawing in FIG. 9, in a state where the distal connection portion 50 is accommodated in the accommodation portion 134, the operation wire 20 is drawn to the proximal side in the forward/backward movement direction. In this manner, the first inclined surface 52 causes the protruding portion 140 to be deformed outward.

One or both of the first inclined surface 52 and the second inclined surface 54 may be a flat surface or a curved surface. In a case of the curved surface, the curved surface may be a convex surface bulging outward in the radial direction so that the protruding portion 140 can be preferably spread outward.

At least one of the first inclined surface 52 and the second inclined surface 54 has a conical shape. A specific shape of the conical surface is not particularly limited. However, for example, it is possible to employ a truncated cone or a truncated pyramid. The first inclined surface 52 or the second inclined surface 54 has the conical shape. Accordingly, when the distal connection portion 50 is removed from the locking portion 130 or inserted into the locking portion 130, it is unnecessary to align the distal connection portion 50 with the locking portion 130, or an angle for alignment can be reduced.

In particular, both the first inclined surface 52 and the second inclined surface 54 according to the present embodiment have the conical surface. More specifically, the first inclined surface 52 is a frusto-conical surface whose diameter decreases toward the proximal side, and the second inclined surface 54 is a conical surface whose diameter decreases toward the distal side. In this manner, the distal connection portion 50 does not need to be aligned with the locking portion 130, and the distal connection portion 50 can be inserted into and removed from the locking portion 130.

As illustrated in FIG. 4, the distal portion of the operation wire 20 has a cylindrical sleeve (diameter reduction sleeve 70) which can be accommodated inside the sheath 10 and which accommodates the distal connection portion 50. As illustrated in FIG. 9B, the inner diameter of at least a portion of the diameter reduction sleeve 70 is smaller than the outer diameter of the locking portion 130 when the distal connection portion 50 is drawable from the accommodation portion 134.

Figure 6:
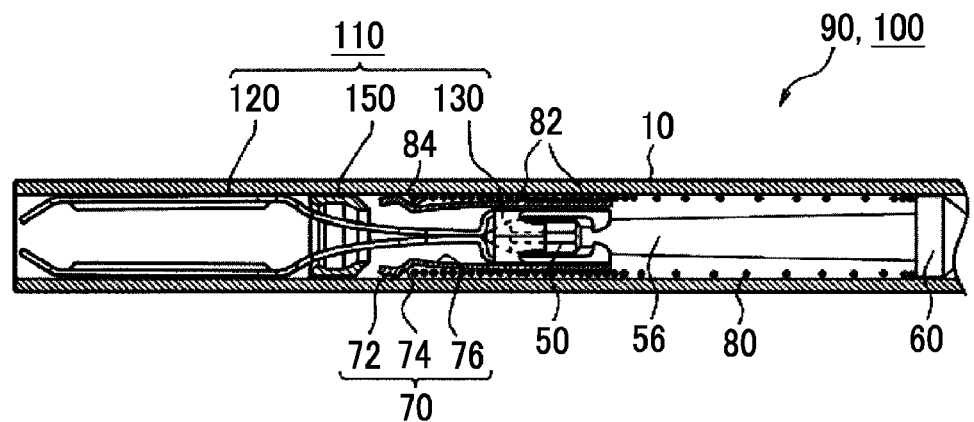
FIG. 6 is a view for describing a state where the clip is accommodated in a sheath.
Figure 7:
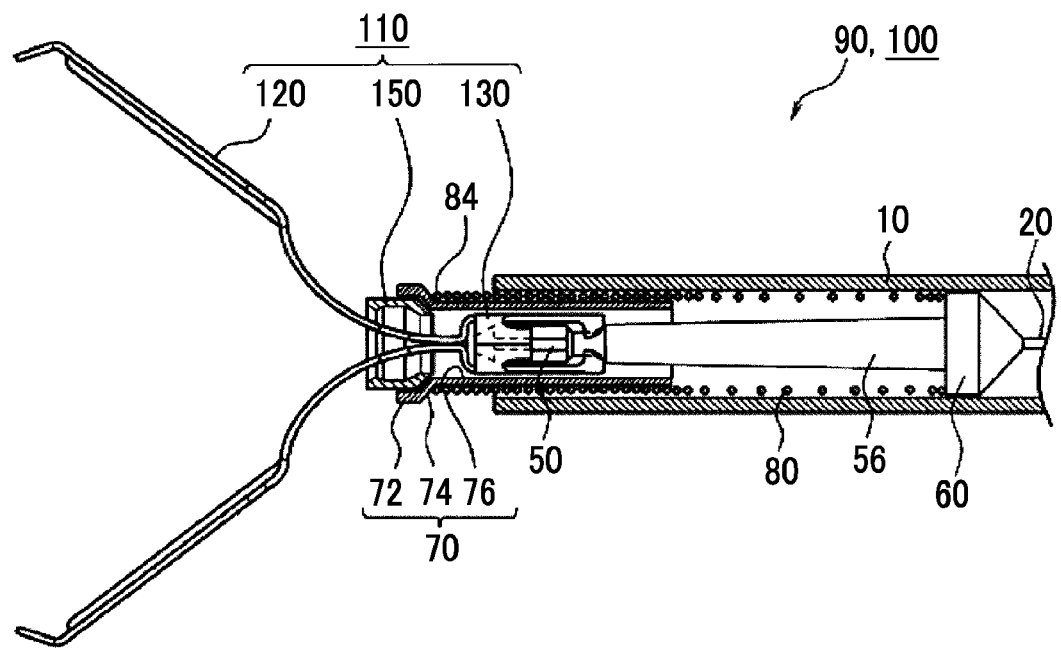
FIG. 7 is a view for describing a state where the clip is protruded and opened from the sheath.
Figure 8:
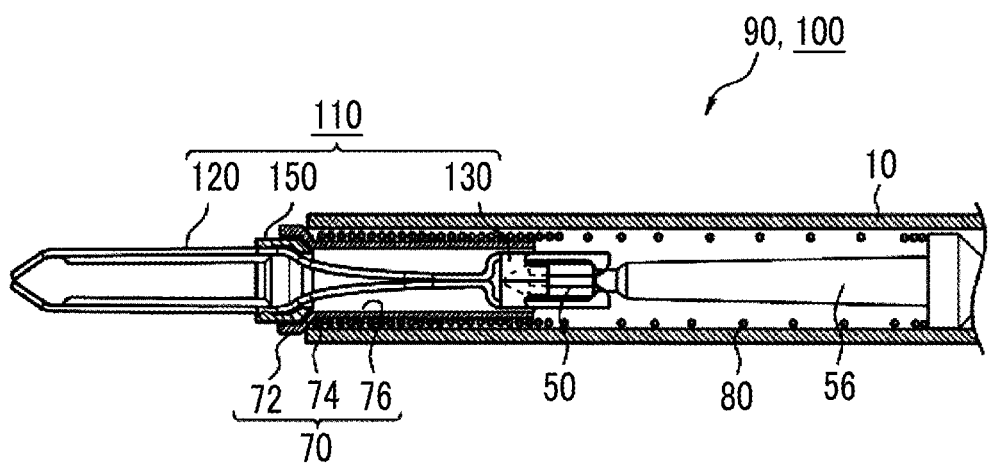
FIG. 8 is a view for describing a ligation state of the clip.

The diameter reduction sleeve 70 is a member for regulating the clamping member 150 moving backward to the sheath 10 and switching the clip 110 (refer to FIG. 7) from an opened state to a closed state (refer to FIG. 8). As illustrated in FIG. 6, the diameter reduction sleeve 70 can be accommodated inside the sheath 10, and causes the operation wire 20 to move forward. In this manner, a portion (diameter enlargement portion 72) of the diameter reduction sleeve 70 can protrude from the sheath 10 (refer to FIGS. 7 to 9).

The sleeve (diameter reduction sleeve 70) according to the present embodiment has a diameter enlargement portion 72, a diameter reduction step portion 74, and a sleeve body 76. The diameter enlargement portion 72 is disposed on the distal side in the diameter reduction sleeve 70, and is elastically self-openable. The diameter reduction step portion 74 is disposed on the proximal side of the diameter enlargement portion 72. The sleeve body 76 is disposed on the proximal side from the diameter reduction step portion 74, and is more rigid in the radial direction than the diameter enlargement portion 72. As illustrated in FIG. 9B, the inner diameter of the sleeve body 76 is smaller than the outer diameter of the locking portion 130 when the distal connection portion 50 is drawable from the accommodation portion 134. In this manner, at least a portion of the protruding portion 140 and the projection piece 142 is moved backward from the sleeve body 76. Accordingly, the projection piece 142 is sufficiently deformed so that the distal connection portion 50 is drawable from the accommodation portion 134. In other words, in a state where the protruding portion 140 and the projection piece 142 are accommodated in the sleeve body 76, the sleeve body 76 constrains the outward deformation of the projection piece 142. Therefore, the distal connection portion 50 is prevented from being separated from the accommodation portion 134.

The diameter reduction step portion 74 is formed in a tapered shape whose diameter decreases toward the proximal side, between the sleeve body 76 and the diameter enlargement portion 72. A configuration material of the diameter reduction sleeve 70 is not limited to a specific material as long as the diameter of the member can decrease by an external force. For example, a metal material, or an elastomer such as a resin or rubber can be used.

The diameter reduction sleeve 70 according to the present embodiment is a cylindrical body (pipe) made of a metal material such as stainless steel, and has one or more slits (not illustrated) formed being cut out from the distal end toward the proximal side of the diameter enlargement portion 72. The slit may be prepared to have a length leading to the diameter reduction step portion 74. Since the slit is provided, at least the diameter enlargement portion 72 of the diameter reduction sleeve 70 of is configured so that the diameter can be deformed to increase or the diameter can be deformed to decrease. As illustrated in FIG. 6, in a state where the diameter reduction sleeve 70 is accommodated in the sheath 10, the diameter of the diameter enlargement portion 72 is deformed to further decrease compared to a natural state (refer to FIG. 4), and thus, the outer diameter is smaller the inner diameter of the sheath 10.

Then, as illustrated in each of FIGS. 7 to 9, the diameter enlargement portion 72 of the diameter reduction sleeve 70 protrudes from the sheath 10 to the distal side. In this manner, the diameter enlargement portion 72 is elastically restored to the natural state. The diameter of the diameter enlargement portion 72 in the natural state is larger than the inner diameter of the sheath 10. In addition, the diameter of the sleeve body 76 in the natural state is smaller than the inner diameter of the sheath 10. The diameter reduction step portion 74 in the natural state has a larger diameter portion and a smaller diameter portion than the inner diameter of the sheath 10.

As illustrated in FIG. 8, the diameter enlargement portion 72 can accommodate the clamping member 150. In other words, the inner diameter of the diameter enlargement portion 72 in the natural state is slightly larger than the outer diameter of the clamping member 150. Then, since the diameter enlargement portion 72 accommodates the clamping member 150, the deformation to decrease the diameter of the diameter enlargement portion 72 is regulated, thereby preventing the diameter enlargement portion 72 from entering the sheath 10. That is, the diameter reduction step portion 74 is locked to the distal end of the sheath 10, thereby regulating the backward movement of the diameter reduction sleeve 70. Accordingly, the clip 110 is drawn using the operation wire 20, thereby enabling the arm 120 of the clip 110 to move backward relative to the diameter enlargement portion 72 and the clamping member 150. In this manner, the arm 120 of the clip 110 is closed. Furthermore, the operation wire 20 can be removed from the clip 110.

In a case where the clamping member 150 is not accommodated in the diameter enlargement portion 72, if the operation wire 20 is moved backward, the diameter enlargement portion 72 is accommodated again in the sheath 10 while being deformed to decrease the diameter.

The elastic portion 80 is a member for connecting the centering portion 60 and the diameter reduction sleeve 70 to each other, and is configured to be extendible in the axial direction.

The elastic portion 80 can be configured to comprise a coil around which a metal or a resin wire material is spirally wound, or an elastomer such as rubber. As the wire material, a metal wire of stainless steel or tungsten can be preferably used. The elastic portion 80 according to the present embodiment is a coil wound at unequal pitches in which a winding pitch of both end portions respectively fixed to the elastic portion 80 and the diameter reduction sleeve 70 is decreased and a winding pitch in the intermediate portion is increased compared to both end portions. More specifically, both end portions of the elastic portion 80 are closely wound so that adjacent winding loops are in contact with each other. The intermediate portion of the elastic portion 80 is wound at winding pitches in which the adjacent winding loops are separated from each other.

The diameter reduction sleeve 70 is a tubular member fixed to the elastic portion 80, and the operation wire 20, the elastic portion 80, and the diameter reduction sleeve 70 are arranged coaxially with the sheath 10. The sleeve body 76 of the diameter reduction sleeve 70 is accommodated in the elastic portion 80 (coil). The distal end of the elastic portion 80 is in contact with the proximal side of the diameter reduction step portion 74. The distal portion of the elastic portion 80 includes a stationary wire 82 fixed to the periphery of the sleeve body 76, and a movable wire 84 located on the distal side of the stationary wire 82 and mounted on the periphery of the sleeve body 76 so as not to be fixed thereto. The stationary wire 82 is fixed to the periphery of the sleeve body 76 using an adhesive, a soldering metal wax, or by means of welding.

Referring to FIGS. 5A and 5B to 9A and 9B, a series of procedures will be described from when the distal connection portion 50 of the operation wire 20 is connected to the clip 110 so as to close the clip 110 until the distal connection portion 50 is further separated from the clip 110.

Figure 5A:
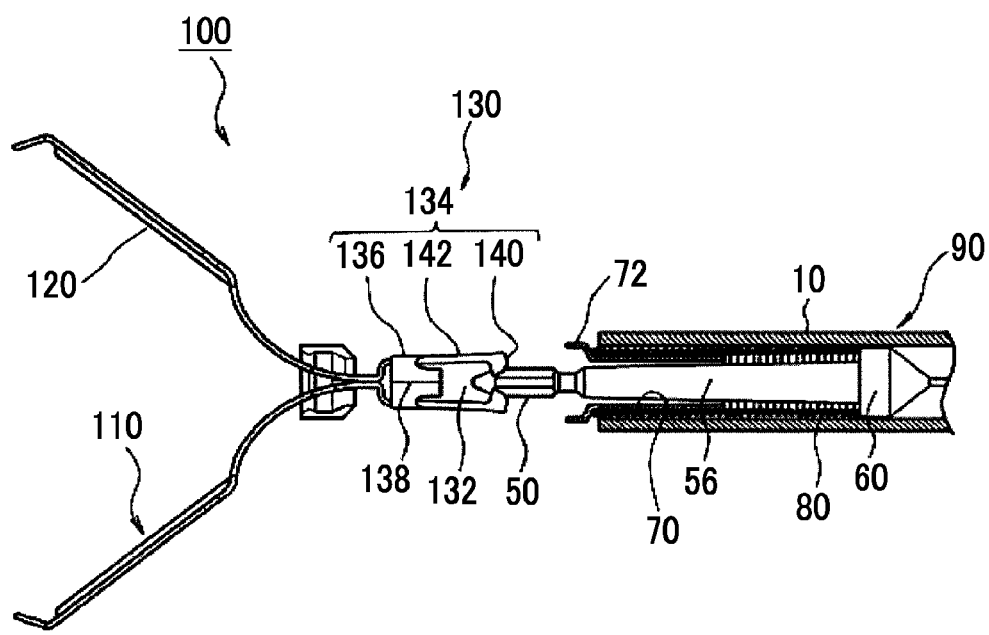
FIG. 5A is a view for describing a state where a distal connection portion is pushed into and connected to a locking portion of the clip.
Figure 5B:
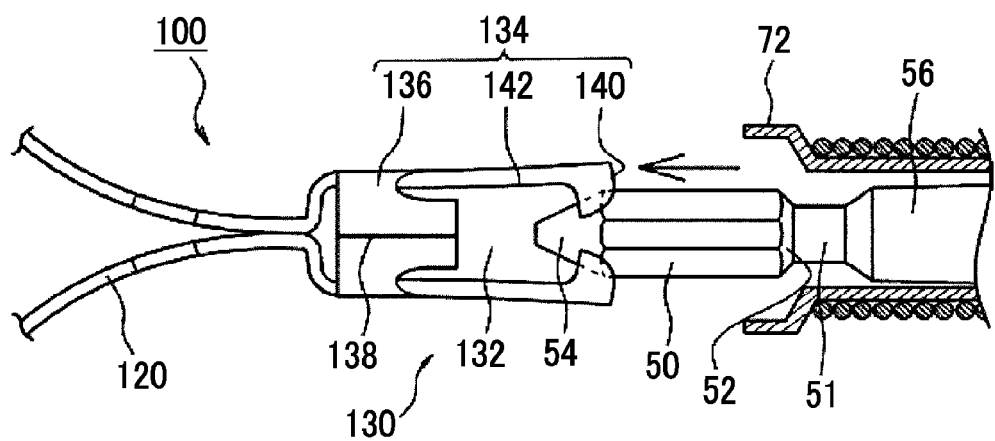
FIG. 5B is an enlarged view of FIG. 5A relating to the vicinity of the distal connection portion.

FIG. 5A is a view for describing a state where the distal connection portion 50 is pushed into and connected to the locking portion 130 of the clip 110. FIG. 5B is an enlarged view of FIG. 5A relating to the vicinity of the distal connection portion 50. FIG. 6 is a view for describing a state where the clip 110 is accommodated in the sheath 10. FIG. 7 is a view for describing a state where the clip 110 is protruded from the sheath 10 and is brought into an opened state. FIG. 8 is a view for describing a ligation state of the clip 110. FIG. 9A is a view for describing a state where the distal connection portion 50 is drawn out from the locking portion 130 of the clip 110. FIG. 9A is an enlarged view of FIG. 9A relating to the vicinity of the distal connection portion 50.

The clip 110 is provided while being accommodated in a cartridge (not illustrated) in a state where the clamping member 150 is mounted on the outer periphery of the arm 120 (refer to each drawing in FIG. 3). The cartridge may have an accommodation portion for the clip 110, and an opening which allows an access to the locking portion 130 of the clip 110 accommodated in the accommodation portion from the outside. Then, the distal connection portion 50 of the operation wire 20 is pushed against the locking portion 130 of the clip 110 accommodated in the cartridge from the proximal side, thereby connecting the operation wire 20 and the clip 110 to each other.

Specifically, as illustrated in FIG. 5A, the distal connection portion 50 of the operation wire 20 is pushed against the protruding portion 140 of the locking portion 130 from the proximal side. In this manner, the protruding portion 140 is elastically deformed outward, and the accommodation portion 134 is opened so that the distal connection portion 50 can be accommodated in the forward/backward movement direction of the operation wire 20. In this case, the slider 94 (refer to FIG. 1) of the treatment instrument body 90 may be operated to move forward so that the distal connection portion 50 protrudes from the distal end of the sheath 10 as illustrated in FIG. 5A. In addition, the protruding portion 140 is elastically deformed outward. In a state where the accommodation portion 134 is opened, as indicated by an arrow in FIG. 5B, the distal connection portion 50 passes through the protruding portion 140 on the distal side in the forward/backward movement direction. The protruding portion 140 is elastically restored inward (refer to FIG. 6). In this manner, the protruding portion 140 is locked to the distal connection portion 50, thereby connecting the distal connection portion 50 and the locking portion 130 to each other.

Here, the description that the protruding portion 140 is elastically deformed outward is not limited to a state where the protruding portion 140 is completely elastically deformed, and includes a state where the protruding portion 140 is elastically deformed together with plastic deformation. In addition, the description that the protruding portion 140 is elastically restored inward includes not only a state where the displacement of the protruding portion 140 which is elastically deformed outward is completely restored, but also a state where the displacement of the outward elastic deformation is partially restored. When the protruding portion 140 is deformed outward by pushing the distal connection portion 50 against the protruding portion 140, the protruding portion 140 is elastically deformed so that the displacement is at least partially restored. That is, the protruding Portion 140 is biased by the distal connection portion 50 so as to open the accommodation portion 134. Then, after the distal connection portion 50 is accommodated in the accommodation portion 134, the protruding portion 140 can be elastically restored, and can close the accommodation portion 134. Therefore, according to the endoscopic clip device 100 of the present embodiment, the operation wire 20 is moved forward, and the distal connection portion 50 is pushed against the axis of the locking portion 130. In this simple manner, the distal connection portion 50 is accommodated in the accommodation portion 134, and is connected to the clip 110. In addition, the protruding portion 140 is formed in a partially arc shape, and the pair of protruding portions 140 is locked to the distal connection portion 50 so that the protruding portions 140 hold the proximal portion of the distal connection portion 50, specifically, the periphery of the neck portion 51. In this manner, the distal connection portion 50 accommodated in the accommodation portion 134 is prevented from being shaken inside the accommodation portion 134.

Specifically, the second inclined surface 54 of the distal connection portion 50 is pushed against the protruding portion 140 from the proximal side. In this manner, the second inclined surface 54 having a normal line which extends obliquely outward toward the distal side pushes the protruding portion 140 outward in the radial direction so that the projection piece 142 is bent and deformed outward. Since the second inclined surface 54 has a conical shape, the second inclined surface 54 is moved forward so that the protruding portion 140 is gradually and strongly biased. Therefore, the protruding portion 140 or the projection piece 142 from being plastically deformed after an impact force is applied thereto.

In a state illustrated in FIG. 5A, the operation wire 20 is further moved forward, the distal connection portion 50 is completely accommodated inside the accommodation portion 134, and thereafter, the operation wire 20 is moved backward. In this manner, as illustrated in FIG. 6, the clip 110 and the diameter reduction sleeve 70 are accommodated inside the sheath 10. In this case, an external force is applied to the diameter enlargement portion 72 of the diameter reduction sleeve 70 so that the diameter enlargement portion 72 is deformed to decrease the diameter. More specifically, the distal connection portion 50 is connected to the locking portion 130 inside the cartridge, and then, the operation wire 20 is moved backward. When the clip 110 is removed from the cartridge, it is preferable that the diameter enlargement portion 72 is biased inward in the radial direction by a specific portion of the cartridge. The outer diameter of the diameter enlargement portion 72 which is deformed to decrease the diameter is smaller than the inner diameter of the sheath 10.

As illustrated in FIG. 6, in a state where the clip 110 is accommodated in the sheath 10, the sheath 10 is caused to penetrate into the body lumen through the forceps hole of the endoscope. If the distal side end portion of the sheath 10 reaches the vicinity of the living body tissue requiring ligation, the operation wire 20 is pushed to the distal side. In this manner, the clip 110 and the clamping member 150 protrude from the distal end of the sheath 10 as illustrated in FIG. 7. The clip 110 is naturally spread to have the maximum opening width by the self-openable force.

In this case, at least the diameter enlargement portion 72 and the diameter reduction step portion 74 in the diameter reduction sleeve 70 protrude from the distal opening of the sheath 10, and are deformed to have the diameter in the natural state. That is, the diameter enlargement portion 72 of the diameter reduction sleeve 70 which is deformed to decrease the diameter after being drawn to the sheath 10 protrudes from the distal opening of the sheath 10. In this manner, the diameter enlargement portion 72 is elastically restored to have a large diameter. Then, the clamping member 150 is fitted into the diameter enlargement portion 72. Next, the position and the orientation of the clip 110 are adjusted with respect to the living body tissue to be ligated.

If the treatment instrument body 90 (refer to FIG. 1) is rotated to generate torques, the operation wire 20 and the distal connection portion 50 are rotated to generate torques in conjunction with each other. As described above, the pair of facing projection pieces 142 comes into close contact with or moves close to the outer peripheral surface of the distal connection portion 50, and the distal connection portion 50 transmits the torques to the locking portion 130. As illustrated in FIG. 7, in a state where the distal connection portion 50 is connected to the locking portion 130 of the clip 110, if treatment instrument body 90 is rotated to generate torques, the torques are transmitted to the locking portion 130 of the clip 110 through the distal connection portion 50, and the arm 120 of the clip 110 is also rotated to generate torques. In this manner, the opening direction of the arm 120 can be oriented in a desired direction with respect to the ligation site of the living body tissue.

After the position and the orientation of the clip 110 are determined, the operation wire 20 is drawn to the proximal side in a state where the distal end of the clip 110 is pushed against the ligation site. The clamping member 150 comes into contact with the inner surface of the diameter reduction step portion 74, and is fitted into the diameter enlargement portion 72, thereby regulating the backward movement to the diameter reduction sleeve 70 and the sheath 10. In addition, the clamping member 150 is fitted to the diameter enlargement portion 72. Accordingly, even if an external force is applied to the diameter enlargement portion 72, the diameter enlargement portion 72 is restrained from being deformed to decrease the diameter. Even if the operation wire 20 is drawn to the proximal side with a strong force, the diameter enlargement portion 72 is prevented from being drawn into the sheath 10.

The operation wire 20 and the diameter reduction sleeve 70 are connected to each other by the elastic portion 80. Therefore, even after the diameter reduction sleeve 70 is regulated in the movement to the proximal side relative to the clip device 100, the operation wire 20 is drawn to the proximal side. In this manner, the elastic portion 80 extends, and the distal connection portion 50 can be further drawn to the proximal side inside the sheath 10.

The operation wire 20 is drawn to the proximal side in the forward/backward movement direction in a state where the distal connection portion 50 is accommodated in the accommodation portion 134. In this manner, as illustrated in FIG. 8, the arm 120 is closed so as to grip the living body tissue. More specifically, if the operation wire 20 is further drawn in a state where the diameter reduction sleeve 70 and the clamping member 150 are regulated in the movement to the proximal side relative to the sheath 10, the arm 120 is drawn into the clamping member 150 and closed. However, the operation wire 20 stops drawing the arm 120 while the arm 120 is closed, and the operation wire 20 is pushed again, thereby enabling the arm 120 to be widely opened. Then, after the optimum ligation can be confirmed, if the operation wire 20 is further drawn to the proximal side, the clamping member 150 is fitted to the narrow width portion 123 (refer to each drawing in FIG. 3) disposed in the arm 120, thereby locking the clip 110. In this manner, the clip 110 is brought into a closed state illustrated in FIG. 8.

When the arm 120 is closed to grip the living body tissue, the protruding portion 140 of the locking portion 130 is accommodated inside the diameter reduction sleeve 70 (sleeve). In this state, the operation wire 20 is further drawn to the proximal side. In this manner, the protruding portion 140 protrudes to the proximal side from the sleeve body 76 of the diameter reduction sleeve 70, and can be greatly deformed outward. Here, the description that the protruding portion 140 is greatly deformed means that the protruding portion 140 is deformed to have a large diameter until at least the distal connection portion 50 is drawable from the accommodation portion 134.

That is, the operation wire 20 is further drawn in a closed state illustrated in FIG. 8, thereby causing the protruding portion 140 of the locking portion 130 to further protrude to the proximal side than the sleeve body 76 located in the proximal portion of the diameter reduction sleeve 70. In this manner, the sleeve body 76 can no longer constrain a diameter increase in the protruding portion 140 and the projection piece 142. Accordingly, the protruding portion 140 can be greatly deformed to increase the diameter beyond the inner diameter of the sleeve body 76 (refer to each drawing in FIG. 9).

Therefore, the operation wire 20 is further drawn to the proximal side in a state where the arm 120 is closed. In this manner, as illustrated in each drawing of FIG. 9, the distal connection portion 50 causes the protruding portion 140 to be deformed outward so as to open the accommodation portion 134. Accordingly, the distal connection portion 50 is drawable from the accommodation portion 134 in the direction indicated by the arrow. Here, when the protruding portion 140 is deformed outward, the protruding portion 140 may be plastically deformed, or may be elastically deformed.

More specifically, the first inclined surface 52 of the distal connection portion 50 biases the protruding portion 140 outward so as to be elastically deformed. The normal line of the first inclined surface 52 is oriented obliquely outward toward the proximal side. Accordingly, the distal connection portion 50 (first inclined surface 52) is moved backward to the proximal side. In this manner, the protruding portion 140 is displaced outward, and the projection piece 142 is bent and deformed outward.

The distal connection portion 50 has a conical shape, and more specifically has a tapered shape whose diameter decreases to the proximal side. Therefore, regardless of the orientation of the distal connection portion 50 and the protruding portion 140, the distal connection portion 50 is moved backward. In this manner, the protruding portion 140 is gradually biased, and is moved backward from the sleeve body 76. If the protruding portion 140 protrudes to the proximal side of the sleeve body 76, these are deformed outward. Therefore, when the living body tissue is ligated, an operation for moving the slider 94 (refer to FIG. 1) backward is continuously performed, and the slider 94 is further moved backward, thereby removing the distal connection portion 50 from the locking portion 130. In this manner, the clip 110 is detached from the operation wire 20, and is caused to indwell the body lumen in a state where living body tissue is ligated.

Through the above-described operations, a series of procedures is completed from when the distal connection portion 50 is connected to the clip 110 so as to close the clip 110 until the distal connection portion 50 is further separated from the clip 110. The above described procedures are repeated, thereby enabling multiple clips 110 to ligate the living body tissue.

As described above, according to the endoscopic clip device 100 of the present embodiment, the distal connection portion 50 has a chunky shape, and is not substantially deformed. The distal connection portion 50 is connected to the clip 110, the living body tissue is ligated, and further, the distal connection portion 50 is removed from the clip 110. Even if the series of procedures is repeated, the wear of the distal connection portion 50 is minimized. In addition, the distal connection portion 50 (operation wire 20) can be removed without damaging the clip 110. Accordingly, there is no possibility that the clip 110 may partially remain in the removed and collected distal connection portion 50. Then, the accommodation portion 134 can accommodate the distal connection portion 50 in the forward/backward movement direction. Accordingly, the distal connection portion 50 (operation wire 20) and the clip 110 are connected to each other by moving the distal connection portion 50 forward to the accommodation portion 134. This is the same when the operation wire 20 is removed. The accommodation portion 134 is opened, and the distal connection portion 50 is drawable by drawing the operation wire 20 to the proximal side in the forward/backward movement direction. Therefore, the procedure is facilitated, thereby preventing a problem such as infection.

The present invention is not limited to the above-described embodiment, and includes various modifications and improvements as long as the object of the present invention is achieved.

Various configuration elements of the endoscopic clip device 100 and the clip 110 according to the present invention do not need to exist individually and independently. The present invention allows that a plurality of configuration elements are formed as a single member, that one element is formed of a plurality of members, that a certain configuration element is a portion of the other configuration element, and that a portion of a certain configuration element overlaps a portion of the other configuration element.

Figure 10:
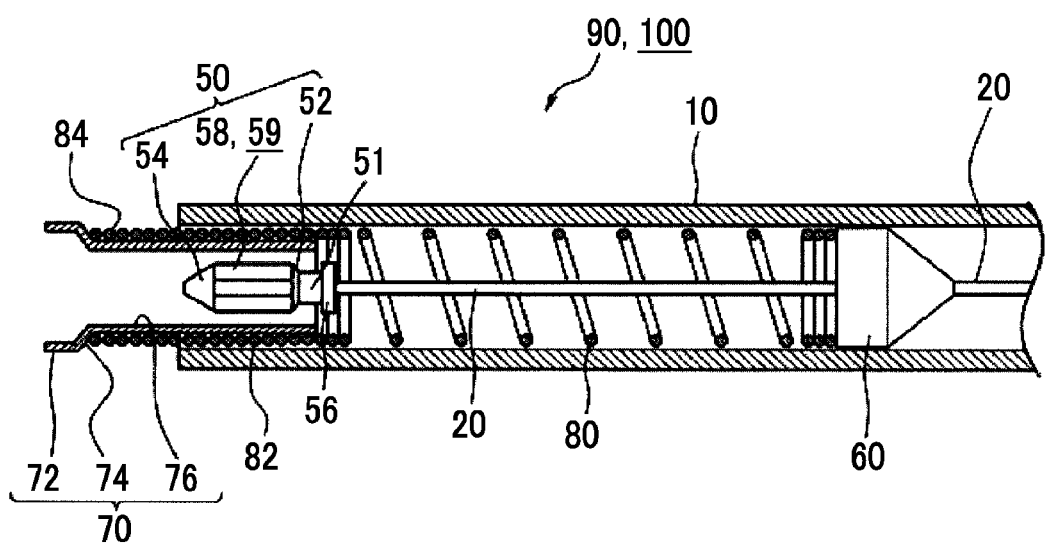
FIG. 10 is a view for describing the distal portion of the treatment instrument body in the first embodiment according to a second aspect of the present invention.

Next, the first embodiment according to a second aspect of the present invention will be described. Points the same as those according to the first aspect will be basically omitted in description, and points different from those according to the first aspect will be mainly described. FIG. 10 is a view for describing the distal portion of the treatment instrument body 90, and is a schematic longitudinal sectional view of the treatment instrument body 90 which is taken along the axial direction.

In FIG. 10, for the sake of convenience, the sheath 10, the diameter reduction sleeve 70, and the elastic portion 80 are hatched in a cross section, and the operation wire 20, a distal connection portion 50, and the centering portion 60 are illustrated using a side view. The description subsequent to FIGS. 11A and 11B will be the same as above. In FIGS. 12 to 16A and 16B, only an end surface of the elastic portion 80 is illustrated, and winding wires appearing behind each drawing are omitted.

The endoscopic clip device (clip device) 100 includes the clip 110 and the treatment instrument body 90. The clip 110 has the plurality of arms 120 for gripping the living body tissue, and the locking portion 130 disposed on the proximal side of the arms 120. On the other hand, as illustrated in FIG. 10, the treatment instrument body 90 has the elongated sheath 10 and the operation wire 20 which is inserted into the sheath 10 so as to be movable forward and backward and which has the distal connection portion 50 disposed in the distal end.

As illustrated in each drawing in FIGS. 2 and 3, the locking portion 130 of the clip 110 has the accommodation portion 134 and the protruding portion 140. The accommodation portion 134 internally has the space 132 for accommodating the distal connection portion 50 of the operation wire 20, and is configured to comprise the plurality of projection pieces 142. The protruding portions 140 are formed to respectively protrude inward in the proximal portions of the plurality of projection pieces 142. The distal connection portion 50 is accommodated in the space 132, thereby connecting the clip 110 and the operation wire 20 to each other.

The locking portion 130 includes the base 136 connected to the proximal end of the arm 120, and the projection piece 142 formed to project from the base 136 to the proximal side and having at least the inner surface side formed flat. A planar portion (outer peripheral surface 58) is formed around the distal connection portion 50. In a state where surfaces of the projection piece 142 and the planar portion (outer peripheral surface 58) are aligned with each other, the distal connection portion 50 is connected to the locking portion 130. In this manner, the projection piece 142 engages with the outer peripheral surface 58 of the distal connection portion 50 rotated to generate torques, and are rotated together with the distal connection portion 50.

As illustrated in each drawing in FIG. 3, in the locking portion 130, the N-number of the projection pieces 142 (N is an integer equal to or more than 2) are arranged apart from each other around the base 136. On the other hand, as illustrated in FIG. 10, the planar portions (outer peripheral surfaces 58) whose number corresponds to an integer multiple of the number N are formed in the distal connection portion 50. In a state where surfaces of the plurality of projection pieces 142 are respectively aligned with surfaces of the planar portions (outer peripheral surfaces 58), the distal connection portion 50 is connected to the locking portion 130. More specifically, in the locking portion 130 according to the present embodiment, two projection pieces 142 are disposed at positions which face each other at 180 degrees on the proximal side of the base 136. That is, the above-described number N satisfies N=2.

On the other hand, the periphery of the distal connection portion 50 according to the present embodiment is formed in a prismatic shape having a rotationally symmetric shape. Specifically, a large diameter body 59 having the largest diameter in the distal connection portion 50 is formed in the prismatic shape having the rotationally symmetric shape. The distal connection portion 50 (large diameter body 59) has a polygonal shape in cross section, and preferably has a regular polygonal shape in cross section. Specifically, the distal connection portion 50 (large diameter body 59) forms a hexagonal prismatic shape having a hexagonal shape in cross section. In the distal connection portion 50 (large diameter body 59), six outer peripheral surfaces 58 which are integral multiples of N=2 are formed. Instead of the present embodiment, the N=3 number of the projection pieces 142 may be equally arranged to face each other at an interval of 120 degrees.

The projection piece 142 according to the present embodiment has a plate shape whose width is narrower than the diameter of the large diameter body 59. A distance between the projection pieces 142 facing each other is set to a dimension which enables the projection pieces 142 to come into close contact with or to move close to the outer peripheral surface 58 of the large diameter body 59. In addition, the projection pieces 142 are disposed so as to face each other, and the number of the outer peripheral surfaces 58 is set to an integer multiple of the projection pieces 142, thereby facilitating the surface alignment between the projection pieces 142 and the outer peripheral surfaces 58. In this manner, even if the distal connection portion 50 is not aligned with the accommodation portion 134, the surface of the projection piece 142 is naturally aligned with the surface of the outer peripheral surface 58 by pushing the distal connection portion 50 into the accommodation portion 134.

In this manner, as will be described later with reference to FIGS. 11B and 15B, when the distal connection portion 50 is inserted into or removed from the accommodation portion 134, the bending stress transmitted from the protruding portion 140 to the projection piece 142 is delivered to the annular base 136 as a deforming force acting in a direction in which the joint of the edges 138 is released. Therefore, the bending stress is consumed as an elastic force for enlarging the base 136, thereby restraining the projection piece 142 from being plastically deformed.

The sheath 10 illustrated in FIG. 10 is a long and flexible tubular member. The sheath 10 is longer than the forceps hole of the endoscope used together with the clip device 100. For example, the sheath 10 can be configured to comprise a coil layer (not illustrated) around which a metal wire is wound long. An inner layer (not illustrated) made of fluorine-based polymer may be disposed on the inner peripheral surface of the coil layer. In addition, the sheath 10 may include a coil layer around which a resin wire is wound, or a flexible resin tube.

The inner diameter dimension of the sheath 10 has a size which slidably accommodates the centering portion 60 (to be described later) disposed in the distal end of the operation wire 20. In the sheath 10 according to the present embodiment, the clip 110 in a closed state can be accommodated inside the sheath 10 (refer to FIG. 12A). Specifically, the inner diameter of the sheath 10 is 100 μm to 2,400 μm, for example. In addition, the thickness dimension of the sheath 10 is 100 μm to 350 μm, for example. In this manner, the flexibility of the sheath 10 can be improved.

The distal connection portion 50 has the first inclined surface 52, the second inclined surface 54, the flange 57, and the neck portion 51 in addition to the large diameter body 59 having the outer peripheral surface 58 described above.

The distal connection portion 50 has a chunky shape having the large diameter body 59 and the neck portion 51 having a diameter smaller than that of the large diameter body 59. The protruding portion 140 is fitted to the neck portion 51 of the distal connection portion 50 accommodated in the accommodation portion 134, thereby connecting the distal connection portion 50 to the locking portion 130.

Here, the description that the distal connection portion 50 has the "chunky shape" means that the distal connection portion 50 is thicker than the locking portion 130, that the distal connection portion 50 is connected to the locking portion 130, and that the displacement of the distal connection portion 50 is sufficiently smaller than the displacement of the locking portion 130 when the distal connection portion 50 is removed from the locking portion 130. A specific shape of the chunky distal connection portion 50 is not particularly limited. As illustrated in FIG. 10, the shape may be a shell shape whose diameter decreases toward the distal side, and may be a columnar shape or a spherical shape.

The first inclined surface 52 is formed on the proximal side of the large diameter body 59, and the diameter thereof decreases toward the proximal side. The normal direction of the first inclined surface 52 is oriented obliquely outward toward the proximal side. In this manner, as will be described later with reference to each drawing in FIG. 16, in a state where the distal connection portion 50 is accommodated in the accommodation portion 134, the operation wire 20 is drawn to the proximal side in the forward/backward movement direction. In this manner, the first inclined surface 52 causes the protruding portion 140 to be deformed outward.

The second inclined surface 54 is formed on the distal side of the large diameter body 59, and the diameter thereof decreases toward the distal side. The normal direction of the second inclined surface 54 is oriented obliquely outward toward the distal side (leftward in FIG. 10). In this manner, as will be described later with reference to each drawing in FIG. 11, the distal connection portion 50 is pushed against the protruding portion 140 from the proximal side. In this manner, the second inclined surface 54 causes the protruding portion 140 to be elastically deformed outward.

The flange 57 is formed to have substantially the same diameter as that of the large diameter body 59, and is formed in the most proximal portion of the distal connection portion 50. The neck portion 51 is formed between the flange 57 and the first inclined surface 52, and the diameter thereof is smaller than that of the flange 57 and the large diameter body 59. The operation wire 20 protrudes from the flange 57 to the proximal side.

As illustrated in FIG. 10, in addition to the distal connection portion 50 described above, the distal portion of the operation wire 20 has the centering portion 60, the elastic portion 80, and the diameter reduction sleeve 70. The centering portion 60 has a chunky shape whose diameter is larger than that of the operation wire 20, and is fixed after the operation wire 20 is inserted on the central axis of the centering portion 60. The centering portion 60 includes a cylinder-shaped portion (cylindrical portion), and the outer diameter of the cylindrical portion is formed to be equal to or slightly smaller than the inner diameter of the sheath 10. As the operation wire 20 moves forward and backward inside the sheath 10, the centering portion 60 moves forward and backward while sliding inside the sheath 10. In this case, since the outer diameter of the centering portion 60 is substantially the same as the inner diameter of the sheath 10, the operation wire 20 moves forward and backward while being positioned in the vicinity of the axis of the sheath 10. Even in a case where the sheath 10 is inserted into the forceps hole of the bent endoscope (not illustrated), since the operation wire 20 is positioned on substantially the center line of the forceps hole, the path length of the operation wire 20 is not changed, thereby restraining the distal connection portion 50 or the clip 110 from unexpectedly protruding from the sheath 10.

Figure 16A:
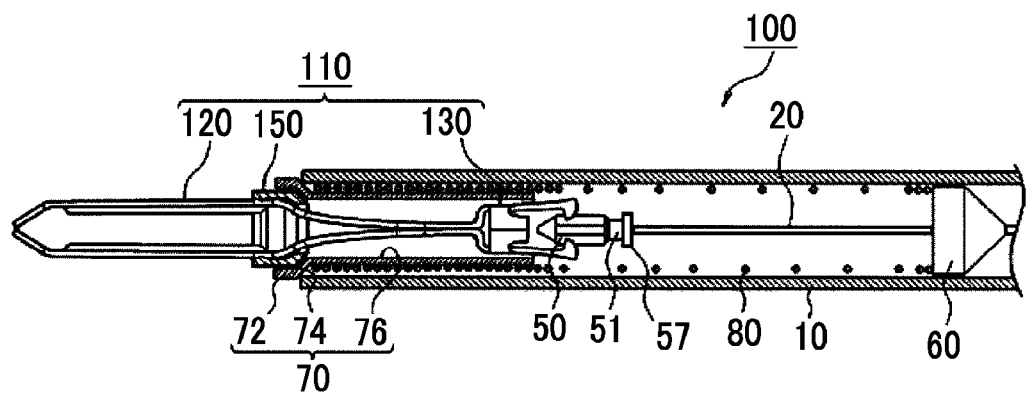
FIG. 16A is a view for describing a state where the distal connection portion is drawn out from the locking portion of the clip.
Figure 16B:
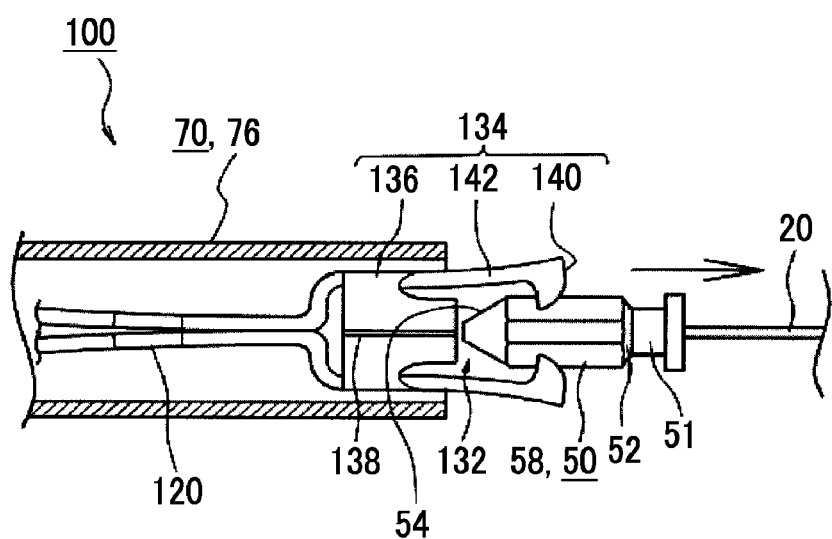
FIG. 16B is an enlarged view of FIG. 16A relating to the vicinity of the distal connection portion.

The diameter reduction sleeve 70 has a tubular shape, can be accommodated inside the sheath 10, and accommodates the distal connection portion 50. As illustrated in FIG. 16B, the inner diameter of at least a portion of the diameter reduction sleeve 70 is smaller than the outer diameter of the locking portion 130 when the distal connection portion 50 is drawable from the accommodation portion 134.

Figure 12:
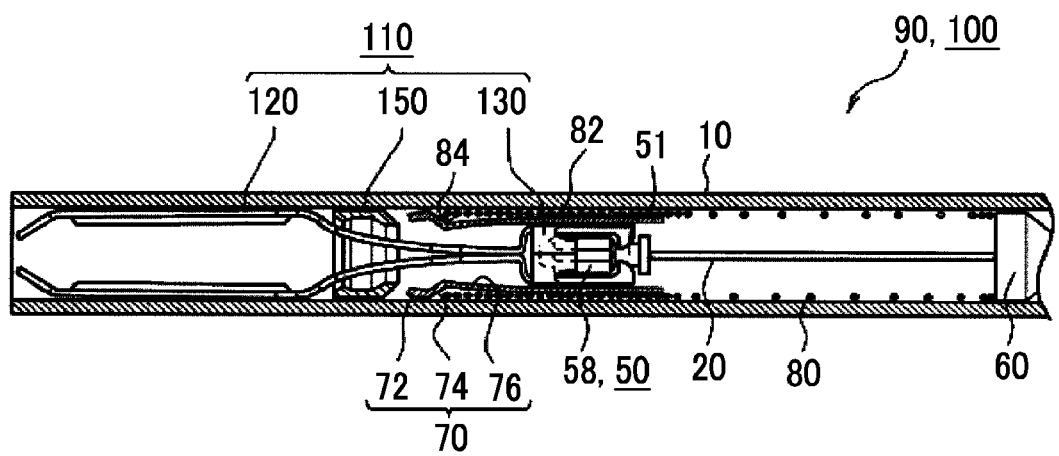
FIG. 12 is a view for describing a state where the clip is accommodated in the sheath.
Figure 14:
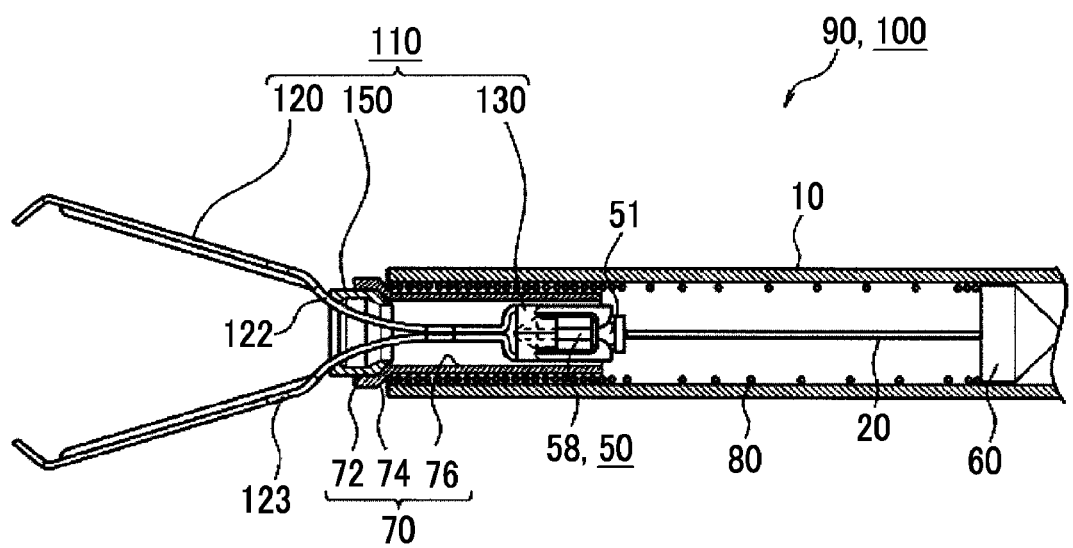
FIG. 14 is a view for describing a state where the clip is closed so that a living body tissue can be gripped again.
Figure 15:
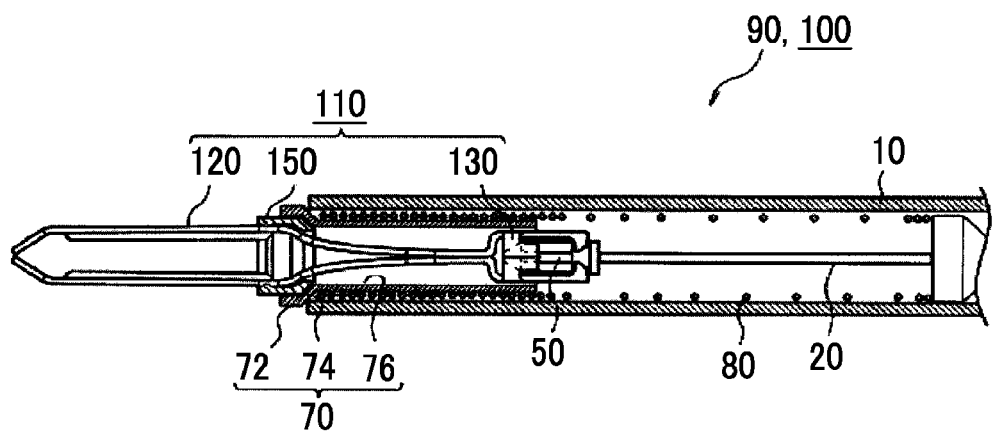
FIG. 15 is a view for describing a ligation state of the clip.

The diameter reduction sleeve 70 is a member for regulating the clamping member 150 moving backward to the sheath 10 and switching the clip 110 (refer to FIG. 13) from an opened state to a closed state (refer to FIG. 15). As illustrated in FIG. 12, the diameter reduction sleeve 70 can be accommodated inside the sheath 10, and causes the operation wire 20 to move forward. In this manner, a portion (diameter enlargement portion 72) of the diameter reduction sleeve 70 can protrude from the sheath 10 (refer to FIGS. 13 to 16).

The sleeve (diameter reduction sleeve 70) according to the present embodiment has the diameter enlargement portion 72, the diameter reduction step portion 74, and the sleeve body 76. The diameter enlargement portion 72 is disposed on the distal side in the diameter reduction sleeve 70, and is elastically self-openable. The diameter reduction step portion 74 is disposed on the proximal side of the diameter enlargement portion 72. The sleeve body 76 is disposed on the proximal side from the diameter reduction step portion 74, and is more rigid in the radial direction than the diameter enlargement portion 72. The inner peripheral surface of the sleeve body 76 has a flat cylindrical shape. Therefore, as will be described later, the friction occurring when the locking portion 130 and the distal connection portion 50 are rotated to generate torques inside the sleeve body 76 is reduced.

As illustrated in FIG. 16B, the inner diameter of the sleeve body 76 is smaller than the outer diameter of the locking portion 130 when the distal connection portion 50 is drawable from the accommodation portion 134. In this manner, at least a portion of the protruding portion 140 and the projection piece 142 is moved backward from the sleeve body 76. Accordingly, the projection piece 142 is sufficiently deformed so that the distal connection portion 50 is drawable from the accommodation portion 134. In other words, in a state where the protruding portion 140 and the projection piece 142 are accommodated in the sleeve body 76, the sleeve body 76 constrains the outward deformation of the projection piece 142. Therefore, the distal connection portion 50 is prevented from being separated from the accommodation portion 134.

The diameter reduction sleeve 70 according to the present embodiment is a cylindrical body (pipe) made of a metal material such as stainless steel, and has one or more slits (not illustrated) formed being cut out from the distal end toward the proximal side of the diameter enlargement portion 72. The slit may be prepared to have a length leading to the diameter reduction step portion 74. Since the slit is provided, at least the diameter enlargement portion 72 of the diameter reduction sleeve 70 of is configured so that the diameter can be deformed to increase or the diameter can be deformed to decrease. As illustrated in FIG. 12, in a stale where the diameter reduction sleeve 70 is accommodated in the sheath 10, the diameter of the diameter enlargement portion 72 is deformed to further decrease compared to a natural state (refer to FIG. 10), and thus, the outer diameter is smaller the inner diameter of the sheath 10.

Then, as illustrated in each of FIGS. 13 to 16, the diameter enlargement portion 72 of the diameter reduction sleeve 70 protrudes from the sheath 10 to the distal side. In this manner, the diameter enlargement portion 72 is elastically restored to the natural state. The diameter of the diameter enlargement portion 72 in the natural state is larger than the inner diameter of the sheath 10. In addition, the diameter of the sleeve body 76 in the natural state is smaller than the inner diameter of the sheath 10. The diameter reduction step portion 74 in the natural state has a larger diameter portion and a smaller diameter portion than the inner diameter of the sheath 10.

As illustrated in FIG. 15, the diameter enlargement portion 72 can accommodate the clamping member 150. In other words, the inner diameter of the diameter enlargement portion 72 in the natural state is slightly larger than the outer diameter of the clamping member 150. Then, since the diameter enlargement portion 72 accommodates the clamping member 150, the deformation to decrease the diameter of the diameter enlargement portion 72 is regulated, thereby preventing the diameter enlargement portion 72 from entering the sheath 10. That is, the diameter reduction step portion 74 is locked to the distal end of the sheath 10, thereby regulating the backward movement of the diameter reduction sleeve 70. Accordingly, the clip 110 is drawn using the operation wire 20, thereby enabling the arm 120 of the clip 110 to move backward relative to the diameter enlargement portion 72 and the clamping member 150. In this manner, the arm 120 of the clip 110 is closed. Furthermore, the operation wire 20 can be removed from the clip 110.

The elastic portion 80 is a member for connecting the centering portion 60 and the diameter reduction sleeve 70 to each other, and is configured to be extendible in the axial direction. The elastic portion 80 is disposed around the operation wire 20 located on the distal side from the centering portion 60. The distal connection portion 50 in the natural state illustrated in FIG. 10 is located inside the diameter reduction sleeve 70.

Referring to FIGS. 11A and 11B to 16A and 16B, a series of procedures will be described from when the distal connection portion 50 of the operation wire 20 is connected to the clip 110 so as to close the clip 110 until the distal connection portion 50 is further separated from the clip 110.

Figure 11A:
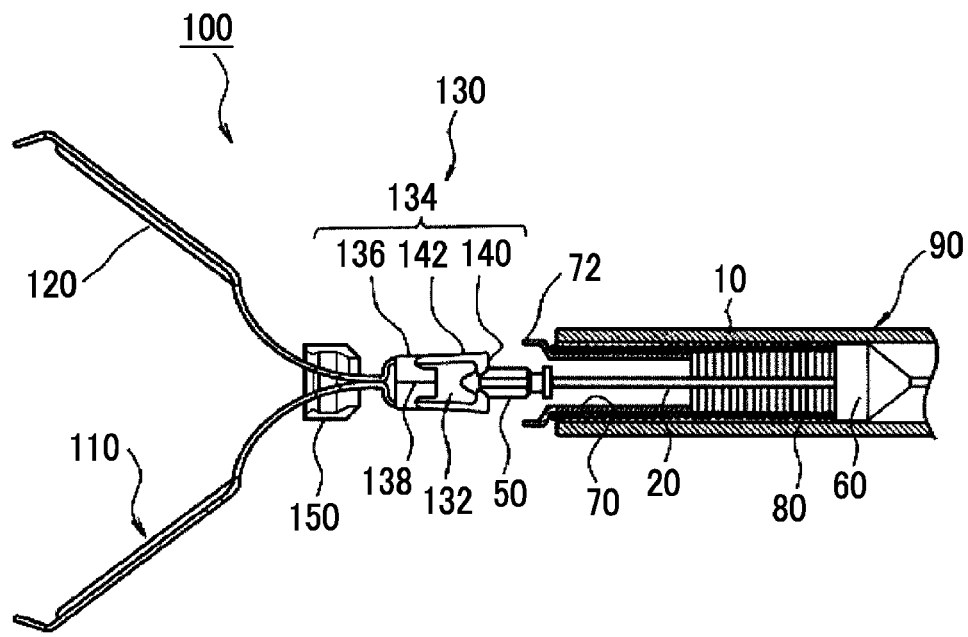
FIG. 11A is a view for describing a state where the distal connection portion is pushed into and connected to the locking portion of the clip.
Figure 11B:
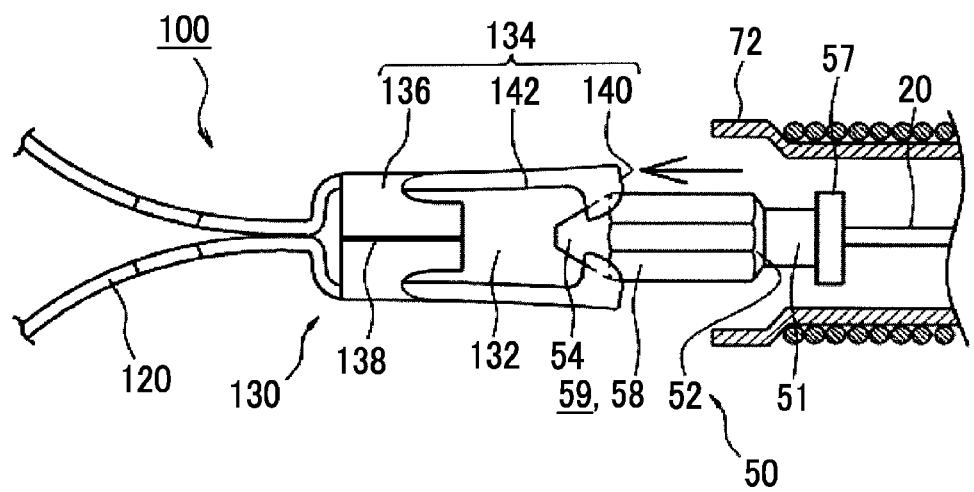
FIG. 11B is an enlarged view of FIG. 11A relating to the vicinity of the distal connection portion.
Figure 13:
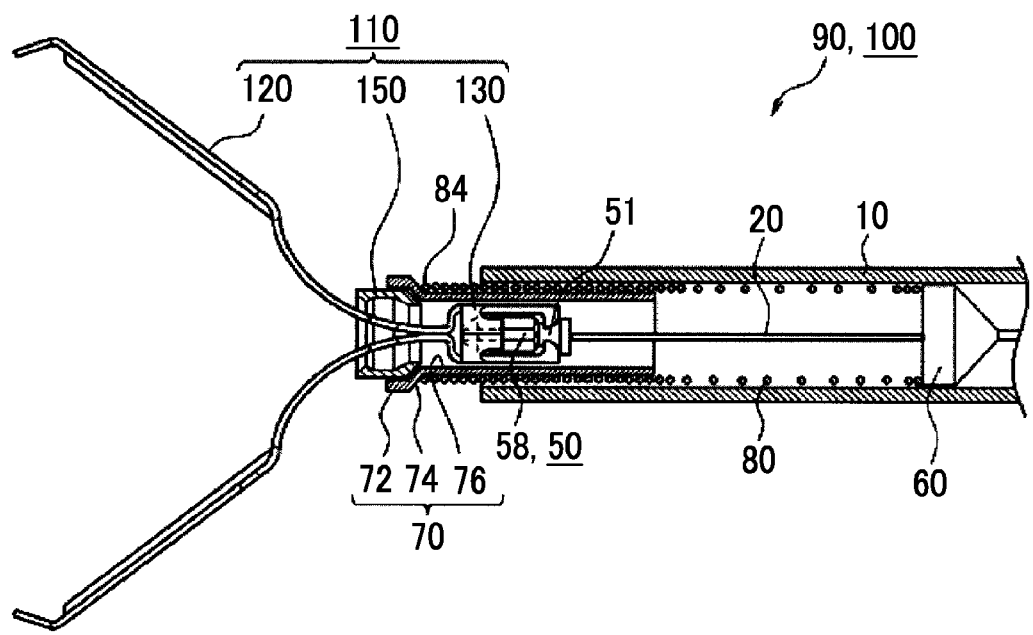
FIG. 13 is a view for describing a state where the clip is protruded and opened from the sheath.

FIG. 11A is a view for describing a state where the distal connection portion 50 is pushed into and connected to the locking portion 130 of the clip 110. FIG. 11B is an enlarged view of FIG. 11A relating to the vicinity of the distal connection portion 50. FIG. 12 is a view for describing a state where the clip 110 is accommodated in the sheath 10. FIG. 13 is a view for describing a state where the clip 110 is protruded from the sheath 10 and is brought into an opened state. FIG. 14 is a view for describing a state where the clip 110 is opened so that the living body tissue can be gripped again. FIG. 15 is a view for describing a ligation state of the clip 110. Then, FIG. 16A is a view for describing a state where the distal connection portion 50 is drawn out from the locking portion 130 of the clip 110. FIG. 16B is an enlarged view of FIG. 16A relating to the vicinity of the distal connection portion 50.

The clip 110 is provided while being accommodated in a cartridge (not illustrated) in a state where the clamping member 150 is mounted on the outer periphery of the arm 120 (refer to each drawing in FIG. 3). The cartridge may have an accommodation portion for the clip 110, and an opening which allows an access to the locking portion 130 of the clip 110 accommodated in the accommodation portion from the outside. Then, the distal connection portion 50 of the operation wire 20 is pushed against the locking portion 130 of the clip 110 accommodated in the cartridge from the proximal side, thereby connecting the operation wire 20 and the clip 110 to each other.

Specifically, as illustrated in FIG. 11A, the distal connection portion 50 of the operation wire 20 is pushed against the protruding portion 140 of the locking portion 130 from the proximal side. In this manner, the protruding portion 140 is elastically deformed outward, and the accommodation portion 134 is opened so that the distal connection portion 50 can be accommodated in the forward/backward movement direction of the operation wire 20. In this case, the slider 94 (refer to FIG. 1) of the treatment instrument body 90 may be operated to move forward so that the distal connection portion 50 protrudes from the distal end of the sheath 10 as illustrated in FIG. 11A. In addition, the protruding portion 140 is elastically deformed outward. In a state where the accommodation portion 134 is opened, as indicated by an arrow in FIG. 11B, the distal connection portion 50 passes through the protruding portion 140 on the distal side in the forward/backward movement direction. The protruding portion 140 is elastically restored inward (refer to FIG. 12). In this manner, the protruding portion 140 is locked to the distal connection portion 50, thereby connecting the distal connection portion 50 and the locking portion 130 to each other.

In a state illustrated in FIG. 11A, the operation wire 20 is further moved forward, the distal connection portion 50 is completely accommodated inside the accommodation portion 134, and thereafter, the operation wire 20 is moved backward. In this manner, as illustrated in FIG. 12, the clip 110 and the diameter reduction sleeve 70 are accommodated inside the sheath 10. In this case, an external force is applied to the diameter enlargement portion 72 of the diameter reduction sleeve 70 so that the diameter enlargement portion 72 is deformed to decrease the diameter. The external force can be applied by the above-described cartridge. More specifically, the distal connection portion 50 is connected to the locking portion 130 inside the cartridge, and then, the operation wire 20 is moved backward. When the clip 110 is removed from the cartridge, it is preferable that the diameter enlargement portion 72 is biased inward in the radial direction by a specific portion of the cartridge. The outer diameter of the diameter enlargement portion 72 which is deformed to decrease the diameter is smaller than the inner diameter of the sheath 10.

As illustrated in FIG. 12, in a state where the clip 110 is accommodated in the sheath 10, the sheath 10 is caused to penetrate into the body lumen through the forceps hole of the endoscope. If the distal side end portion of the sheath 10 reaches the vicinity of the living body tissue requiring ligation, the operation wire 20 is pushed to the distal side. In this manner, the clip 110 and the clamping member 150 protrude from the distal end of the sheath 10 as illustrated in FIG. 7. The clip 110 is naturally spread to have the maximum opening width by the self-openable force.

If the treatment instrument body 90 (refer to FIG. 1) is rotated to generate torques, the operation wire 20 and the distal connection portion 50 are rotated to generate torques in conjunction with each other. As described above, the pair of facing projection pieces 142 comes into close contact with or moves close to the outer peripheral surface 58 of the distal connection portion 50, and the distal connection portion 50 transmits the torques to the locking portion 130. As illustrated in FIG. 13, in a state where the distal connection portion 50 is connected to the locking portion 130 of the clip 110, if treatment instrument body 90 is rotated to generate torques, the torques are transmitted to the locking portion 130 of the clip 110 through the distal connection portion 50, and the arm 120 of the clip 110 is also rotated to generate torques. In this manner, the opening direction of the arm 120 can be oriented in a desired direction with respect to the ligation site of the living body tissue.

The locking portion 130 (projection piece 142) and the distal connection portion 50 (large diameter body 59) are locked and connected to each other around the axis of the operation wire 20. Here, the description that the locking portion 130 and the distal connection portion 50 engage with each other includes not only an aspect in which both of these always engage with each other in a state where the distal connection portion 50 is connected to the locking portion 130, but also an aspect in which the operation wire 20 is rotated to generate torques so that the locking portion 130 and the distal connection portion 50 are locked to each other.

According to the present embodiment, the locking portion 130 and the distal connection portion 50 do not come into frictional contact with each other, but are mechanically locked to each other so as to be rotated to generate torques. Therefore, the torques applied to the treatment instrument body 90 and the operation wire 20 are satisfactorily transmitted to the clip 110.

In addition, the distal portion of the operation wire 20 has the cylindrical diameter reduction sleeve 70 (sleeve) for accommodating the distal connection portion 50. Then, the operation wire 20 is rotated to generate torques, thereby causing the locking portion 130, the distal connection portion 50, and the diameter reduction sleeve 70 to be axially rotated around the axis inside the sheath 10.

In this manner, when the clip 110 in an opened state illustrated in FIG. 13 is oriented in the desired direction by aligning the clip 110 with the living body tissue, the clip 110 is prevented from receiving a frictional force after coming into contact with the inner surface of the sheath 10. In particular, the sheath 10 according to the present embodiment is formed of the coil layer, and irregular winding wires are formed on the inner peripheral surface of the sheath 10. Therefore, the diameter reduction sleeve 70 (the sleeve body 76) is interposed between the clip 110 and the sheath 10, thereby allowing the clip 110 to be smoothly rotated to generate torques.

In addition, the diameter reduction sleeve 70 according to the present embodiment is connected to the centering portion 60 and the operation wire 20 via the elastic portion 80. Therefore, if the operation wire 20 is rotated to generate torques, the diameter reduction sleeve 70 is rotated to generate torques later than the distal connection portion 50 or the locking portion 130. In this manner, a speed difference is generated in the rotation direction between the sheath 10 and the diameter reduction sleeve 70, and between the diameter reduction sleeve 70 and the locking portion 130. Accordingly, the sheath 10 and the diameter reduction sleeve 70, and the diameter reduction sleeve 70 and the locking portion 130 are satisfactorily rotated without coming into close contact with each other.

In a state where the distal connection portion 50 is accommodated in the accommodation portion 134, the operation wire 20 is drawn to the proximal side in the forward/backward movement direction. In this manner, as illustrated in FIG. 14, the arm 120 is slightly closed. In this case, the locking portion 130 and the distal connection portion 50 are located inside the sleeve body 76. The clamping member 150 is located in the proximal portion 122, and does not reach the narrow width portion 123. In this manner, the arm 120 is brought into a semi-ligated state where the arm 120 lightly grips and holds the living body tissue. If it is necessary to grip the living body tissue again in the semi-ligated state, the operation wire 20 is moved forward again. In this manner, the arm 120 is opened by the self-openable force of the arm 120, and the force causes the arm 120 to move forward to the clamping member 150, thereby causing the arm 120 to return to the opened state in FIG. 13. Even in a case where the operation wire 20 is rotated to generate torques in the ligation state illustrated in FIG. 14, the distal connection portion 50 and the locking portion 130 engage with each other. Therefore, the clip 110 can be rotated to generate torques in a desired direction.

After the clip 110 is aligned with the proper position and direction, if the operation wire 20 is greatly moved backward compared to the semi-ligated state, as illustrated in FIG. 15, the arm 120 is closed and the living body tissue is ligated. More specifically, if the operation wire 20 is further drawn in a state where the diameter reduction sleeve 70 and the clamping member 150 are regulated in moving to the proximal side relative to the sheath 10, the arm 120 is drawn into the clamping member 150 and closed. In this case, the clamping member 150 is fitted to the narrow width portion 123 (refer to each drawing in FIG. 3) disposed in the arm 120, and the clip 110 is locked. In this manner, the clip 110 is maintained in the closed state illustrated in FIG. 15.

When the arm 120 is closed so as to ligate the living body tissue, the protruding portion 140 of the locking portion 130 is accommodated inside the diameter reduction sleeve 70 (sleeve). In this state, the operation wire 20 is further drawn to the proximal side. In this manner, the protruding portion 140 protrudes to the proximal side from the sleeve body 76 of the diameter reduction sleeve 70, and can be greatly deformed outward. Here, the description that the protruding portion 140 is greatly deformed means that the protruding portion 140 is deformed to have a large diameter until at least the distal connection portion 50 is drawable from the accommodation portion 134.

That is, the operation wire 20 is further drawn in closed state illustrated in FIG. 15, thereby causing the protruding portion 140 of the locking portion 130 to further protrude to the proximal side than the sleeve body 76 located in the proximal portion of the diameter reduction sleeve 70. In this manner, the sleeve body 76 can no longer constrain a diameter increase in the protruding portion 140 and the projection piece 142. Accordingly, the protruding portion 140 can be greatly deformed to increase the diameter beyond the inner diameter of the sleeve body 76 (refer to each drawing in FIG. 16).

Therefore, the operation wire 20 is further drawn to the proximal side in a state where the arm 120 is closed. In this manner, as illustrated in each drawing of FIG. 16, the distal connection portion 50 causes the protruding portion 140 to be deformed outward so as to open the accommodation portion 134. Accordingly, the distal connection portion 50 is drawable from the accommodation portion 134 in the direction indicated by the arrow. Here, when the protruding portion 140 is deformed outward, the protruding portion 140 may be plastically deformed, or may be elastically deformed.

Hereinafter, a modification example of the distal connection portion 50 will be described with reference to second to fourth embodiments according to the second aspect of the present invention, and repeated description from the first embodiment will be omitted.

Second Embodiment

Figure 17A:
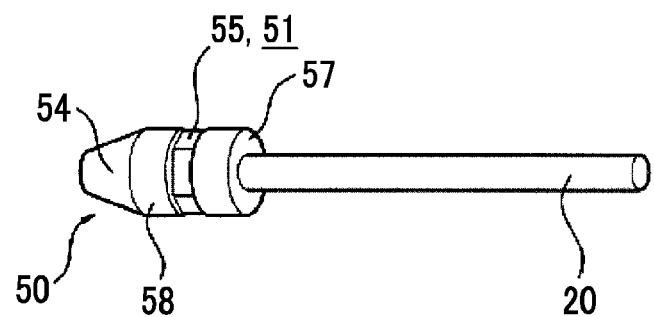
FIG. 17A is a view for describing the distal connection portion in the second embodiment according to the second aspect of the present invention.
Figure 17B:
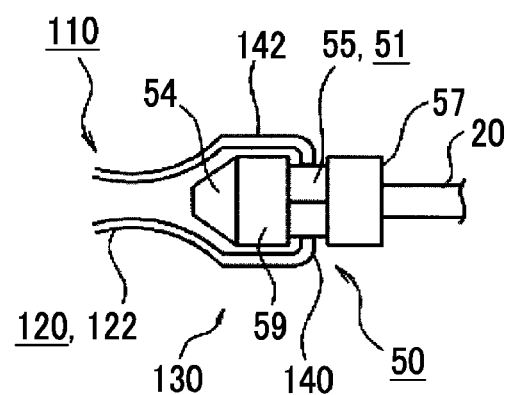
FIG. 17B is a view for describing a state where the distal connection portion in the second embodiment according to the second aspect of the present invention is connected to the locking portion of the clip.

FIG. 17A is a view for describing the distal connection portion 50 according to the second embodiment. FIG. 17B is a view for describing a state where the distal connection portion 50 according to the second embodiment is connected to the locking portion 130 of the clip 110. In each drawing in FIG. 17, only a portion of the operation wire 20 and the clip 110 is illustrated, and other portions are omitted. The same applies to each drawing in FIGS. 18 and 19.

The distal connection portion 50 according to the present embodiment differs from that according to the first embodiment (refer to FIG. 10) in that a planar portion (locking surface 55) is formed around the neck portion 51. As illustrated in FIG. 17B, the distal connection portion 50 is connected to the locking portion 130 in a state where the distal edge of the protruding portion 140 is in contact with the planar portion (locking surface 55).

In the present embodiment, when the operation wire 20 is rotated to generate torques, the projection piece 142 of the locking portion 130 and the neck portion 51 of the distal connection portion 50 are locked to each other, and are integrally rotated. That is, in the first embodiment, the projection piece 142 and the outer peripheral surface 58 of the large diameter body 59 are brought into contact with (locked to) each other so as to transmit the torques. In contrast, in the present embodiment, the locking surface 55 of the neck portion 51 applies the torques to the distal edge of the protruding portion 140. Therefore, the torques can be easily and reliably transmitted by forming the distal edge of the protruding portion 140 into a shape which comes into close contact with the periphery of the neck portion 51.

Third Embodiment

Figure 18A:
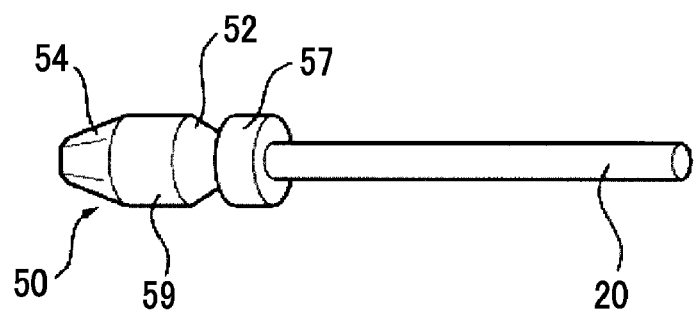
FIG. 18A is a view for describing a distal connection portion in a third embodiment according to the second aspect of the present invention.
Figure 18B:
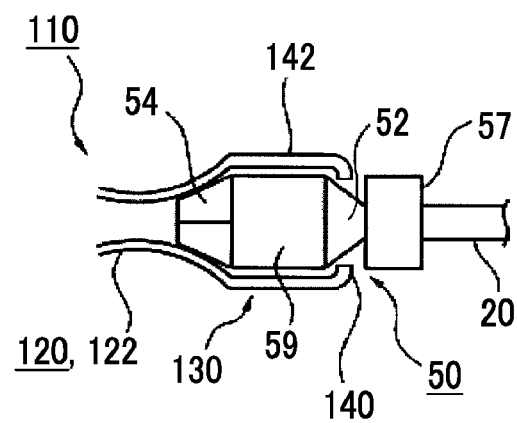
FIG. 18B is a view for describing a state where the distal connection portion in the third embodiment according to the second aspect of the present invention is connected to the locking portion of the clip.

FIG. 18A is a view for describing the distal connection portion 50 according to the third embodiment. FIG. 18B is a view for describing a state where the distal connection portion 50 according to the third embodiment is connected to the locking portion 130 of the clip 110.

The present embodiment is different from the first embodiment (refer to FIG. 10) in that the distal portion of the distal connection portion 50 has a flat inclined surface (second inclined surface 54) whose diameter decreases toward the distal side. That is, the second inclined surface 54 according to the present embodiment has a planar portion. As illustrated in FIG. 18B, in a state where surfaces of the arm 120 (proximal portion 122) of the clip 110 and the inclined surface (second inclined surface 54) are aligned with each other, the distal connection portion 50 is connected to the locking portion 130.

According to the present embodiment, the torques are transmitted from the distal connection portion 50 to the arm 120 (the proximal portion 122) of the clip 110. As illustrated in FIG. 13, in an opened state of the clip 110, the distal connection portion 50 is pushed so as to move forward to the locking portion 130 of the clip 110. In this case, a pushing force is applied from the second inclined surface 54 to the proximal portion 122 so that both of these are in close contact with each other. Therefore, according to the present embodiment, the torques can be satisfactorily transmitted from the distal connection portion 50 to the arm 120 (proximal portion 122).

Fourth Embodiment

Figure 19A:
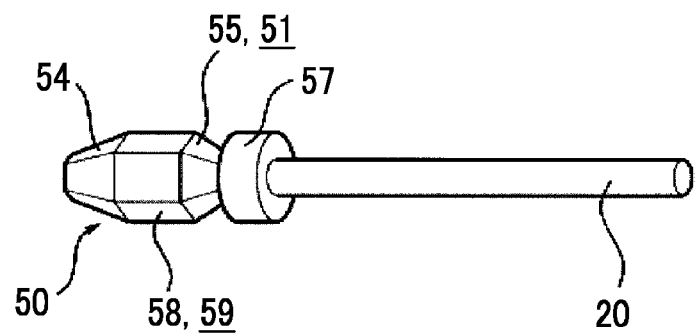
FIG. 19A is a view for describing a distal connection portion in a fourth embodiment according to the second aspect of the present invention.
Figure 19B:
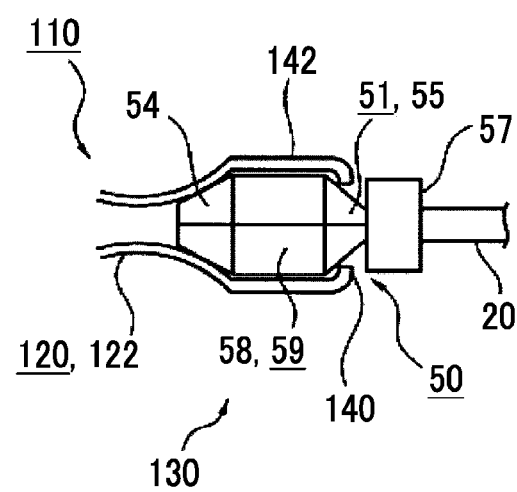
FIG. 19B is a view for describing a state where the distal connection portion in the fourth embodiment according to the second aspect of the present invention is connected to the locking portion of the clip.

FIG. 19A is a view for describing the distal connection portion 50 according to the fourth embodiment. FIG. 19B is a view for describing a state where the distal connection portion 50 according to the fourth embodiment is connected to the locking portion 130 of the clip 110.

The distal connection portion 50 according to the present embodiment has a flat inclined surface (second inclined surface 54) whose diameter decreases toward the distal side on the distal portion as in the third embodiment (refer to FIG. 18A). In addition to this configuration, as in the first embodiment (refer to FIG. 10), the periphery of the large diameter body 59 is formed in a prismatic shape having a rotationally symmetric shape. Furthermore, as in the second embodiment (refer to FIG. 17A), the locking surface 55 is formed around the neck portion 51. In this manner, according to the distal connection portion 50 of the present embodiment, the torques are transmitted to the distal edge of the protruding portion 140 from the locking surface 55 of the neck portion 51. In addition, the torques are transmitted to the projection piece 142 from the outer peripheral surface 58 of the large diameter body 59, and further to the proximal portion 122 of the arm 120 from the second inclined surface 54.

The present invention is not limited to the above-described embodiments, and includes various modifications and improvements as long as the object of the present invention is achieved.

Various configuration elements of the endoscopic clip device 100 according to the present invention do not need to exist individually and independently. The present invention allows that a plurality of configuration elements are formed as a single member, that one element is formed of a plurality of members, that a certain configuration element is a portion of the other configuration element, and that a portion of a certain configuration element overlaps a portion of the other configuration element.

Hereinafter, an embodiment according to the third aspect of the present invention will be described with reference to the drawings. In all of the drawings, the same reference numerals will be given to the same configuration elements, and repeated explanation will be appropriately omitted.

In the present embodiment, some cases will be described in which upward, downward, leftward, and rightward directions are defined as illustrated in the drawing. However, the directions are defined for the sake of convenience in order to briefly describe a relative relationship between configuration elements. The directions do not limit directions at the time of manufacturing or using products which embody the present invention.

Various configuration elements of the endoscopic treatment instrument according to the present invention do not need to exist individually and independently. The present invention allows that a plurality of configuration elements are formed as a single member, that one element is formed of a plurality of members, and that a portion of a certain configuration element overlaps a portion of the other configuration element.

Unless otherwise specified, terms in the present invention or terms used in describing the present invention are defined as follows.

In the present invention, the "self-openable force" means a force which attempts to open itself against an external force for closing.

In describing the present invention, unless otherwise specified, the "distal side" means a side having the distal portion of the endoscopic treatment instrument or the clip mounted thereon. That is, the "distal side" is equal to a side far from the side operated by an operator who operates the endoscopic treatment instrument (hereinafter, simply referred to as an "operator"), and is substantially equal to the distal side of the endoscopic treatment instrument.

In addition, in describing the present invention, unless otherwise specified, the "proximal side" means a side having the proximal portion of the endoscopic treatment instrument or the clip mounted thereon. That is, the "proximal side" is equal to a side close to the side operated by the operator, and is substantially equal to the proximal side of the endoscopic treatment instrument.

In the description of the present invention, unless otherwise specified, the "inside" means a direction toward the axis of the clip or the extension of the axis. In addition, the "outside" means a direction away from the axis of the clip or the extension of the axis.

In addition, in describing the present invention, unless otherwise specified, the "axial direction" means a direction toward the axis of the clip or the extension of the axis, and is substantially equal to the forward-backward movement direction of the operation wire of the endoscopic treatment instrument.

<Outline of Embodiment>

Hereinafter, a configuration of an endoscopic treatment instrument 1100 which is an example of the embodiment according to the present invention will be described with reference to the drawings.

Figure 20:
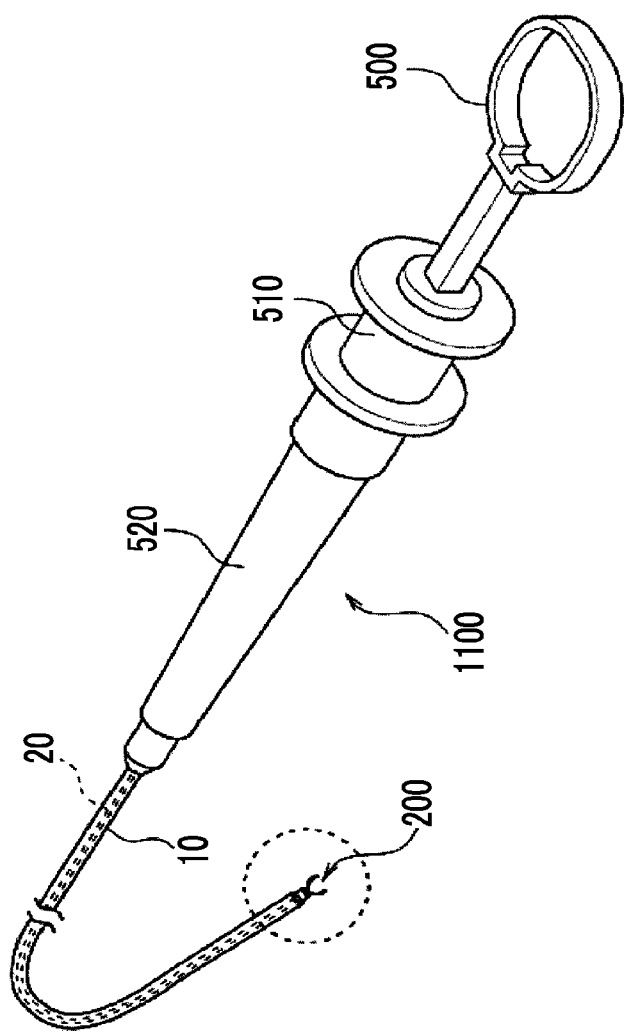
FIG. 20 is a perspective view of an endoscopic treatment instrument which illustrates an embodiment according to a third aspect of the present invention.

FIG. 20 is a perspective view of the endoscopic treatment instrument 1100 illustrating the embodiment of according to the third aspect of the present invention, and illustrates a state where a clip 200 is mounted thereon. As illustrated in FIG. 20, the endoscopic treatment instrument 1100 is used in a state where the clip 200 is mounted on the distal side of the operation wire 20.

For example, the endoscopic treatment instrument 1100 according to the present embodiment is inserted into a channel (not illustrated) of an endoscope (not illustrated), and causes the clip 200 to protrude from the distal portion of the channel. In this manner, the endoscopic treatment instrument 1100 can be used as an elongated medical instrument for ligating the living body tissue inside the body lumen.

The endoscopic treatment instrument 1100 includes the clip 200, the elongated sheath 10, and the operation wire 20 inserted so as to movable forward and a backward inside the sheath 10. In addition, the endoscopic treatment instrument 1100 includes a finger ring 500, a drive unit 510, and an operation unit body 520 from the proximal side.

An operator operates the endoscopic treatment instrument 1100 by moving the drive unit 510 relative to the operation unit body 520, the operation wire 20 inserted into the sheath 10 moves forward and backward in an extension direction of the sheath 10. In addition, a finger is hooked into and fixed the finger ring 500, and the operation unit body 520 is entirely rotated about the axis. In this manner, the operation wire 20 and the clip 200 can be rotated and operated. However, the above-described operation relating to the operation of the endoscopic treatment instrument 1100 is an example of the endoscopic treatment instrument 1100 according to the present embodiment, and does not limit the present invention at all.

Figure 21A:
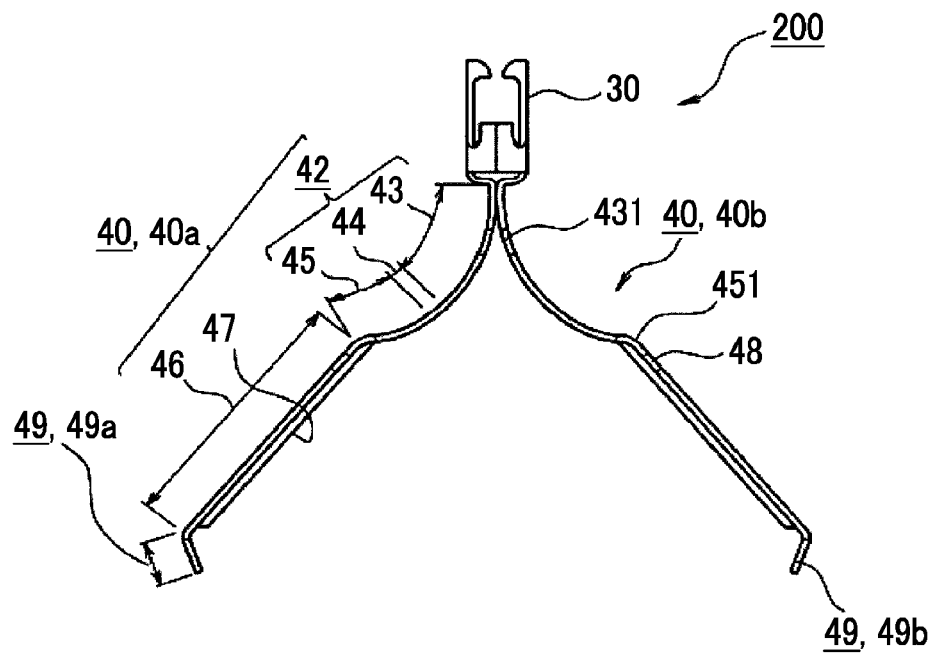
FIG. 21A is a view for describing a state where a clamping member is removed from the clip, and is a front view thereof.
Figure 21B:
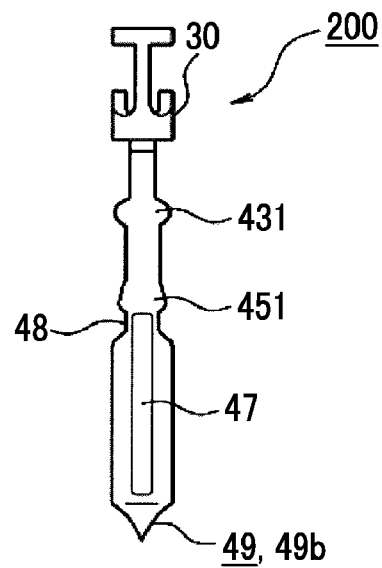
FIG. 21B is a view for describing a state where the clamping member is removed from the clip, and is a side view thereof.
Figure 22A:
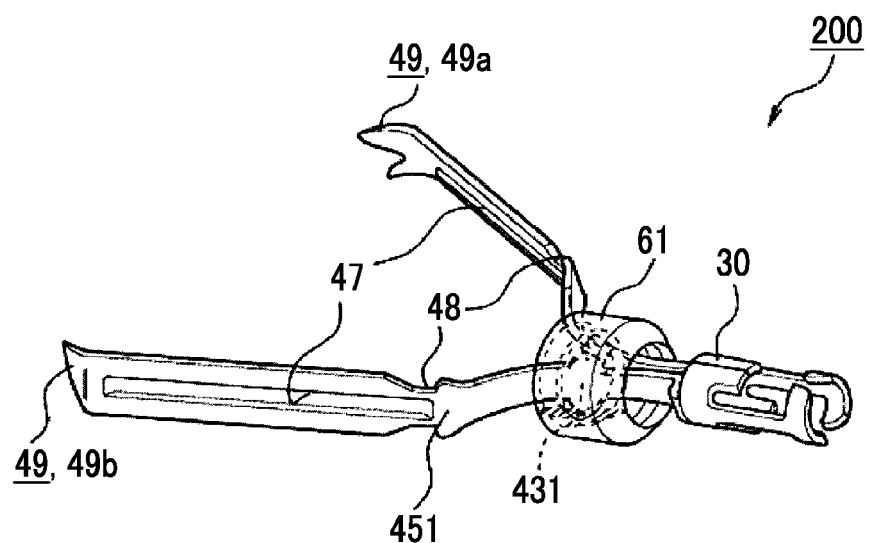
FIG. 22A is a view for describing the clip on which the clamping member is mounted, and is a perspective view when the clip is viewed from a proximal side.

Next, the clip 200 used for the endoscopic treatment instrument 1100 will be described with reference to FIGS. 21A and 21B or FIGS. 22A and 22B. FIGS. 21A and 21B are views for describing a state where a clamping member 61 is removed from the clip 200. FIG. 21A is a front view, and FIG. 21B is a side view. FIG. 22A is a view for describing the clip 200 on which the clamping member 61 mounted. FIG. 21A is a perspective view when the clip 200 is viewed from the proximal side. FIG. 21B is a sectional view of the clamping member 61.

The clip 200 includes a locking portion (first locking portion 30), a plurality of arms (arm 40a and arm 40b), the clamping member 61, and a plurality of claws (distal claw 49a and distal claw 49b).

The first locking portion 30 engages with the distal side of the operation wire (operation wire 20 in FIG. 20).

The plurality of arms 40 are disposed on the distal side from the first locking portion 30, and are opened outward by the self-openable force.

The clamping member 61 internally has the plurality of arms 40 inserted into the clamping member 61, and a position relative to the plurality of arms 40 is displaced from the proximal side to the distal side. In this manner, the plurality of arms 40 are closed inward.

The plurality of distal claws 49 are disposed on the distal side from the plurality of arms 40, and protrude inward.

Each of the arms 40 includes a bending portion 42 which is bent outward so that the curvature radius of the proximal side is larger than the curvature radius of the distal side.

In the clip 200 according to the present embodiment, since the bending portion 42 is bent outward, the arm 40 can be widely opened.

In addition, when the clamping member 61 is displaced from the proximal side to the distal side and the bending portion 42 is closed, the arms 40 are gently closed with respect to the displacement while the clamping member 61 is located on the proximal side (proximal portion 43) of the bending portion 42. Accordingly, the clamping member 61 can seek for the living body tissue serving as a ligation target, while moving forward and backward, thereby further facilitating accurate handling.

Then, while the clamping member 61 is located on the distal side (distal portion 45) of the bending portion 42, the operation load increases than when the clamping member 61 is located on the proximal side (proximal portion 43), thereby reducing the risk that the clamping member 61 may closed due to by a wrong operation.

Since the present embodiment has this configuration, the clip 200 is suitably used for ligation of the living body tissue requiring accurate handling.

As illustrated in FIGS. 21A and 21B, the clip 200 according to the present embodiment has a shape in which the plurality of arms 40 are terminated on the proximal side (toward the first locking portion 30) without intersecting each other. Therefore, the clip 200 is more likely to be miniaturized, compared to the clip having the shape in which the plurality of arms illustrated in PTL 1 intersect each other once on the proximal side. In addition, since the clip having the shape illustrated in PTL 1 has to adopt a configuration in which the clip is bent inward in the vicinity where the plurality of arms intersect each other. Consequently, a portion corresponding to the bending portion 42 according to the present invention is less likely to be disposed in the clip. Therefore, as in the present embodiment, in order to embodying the present invention, it is preferable to employ the shape in which the plurality of arms 40 are terminated on the proximal side without intersecting each other.

<Details of Clip 200>

Next, the clip 200 according to the present embodiment will be described mainly with reference to FIGS. 21A and 21B to FIG. 24.

Figure 22B:
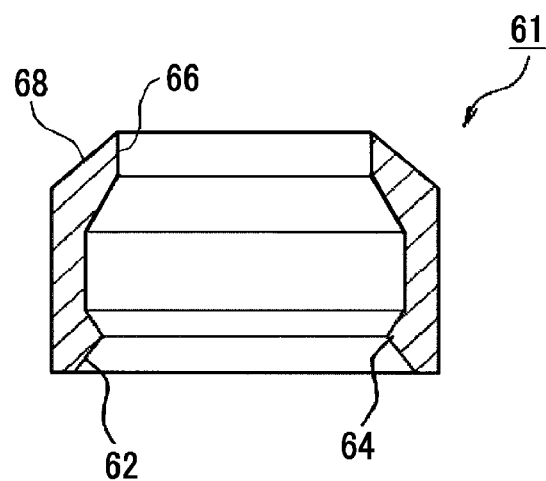
FIG. 22B is a sectional view of the clamping member.
Figure 23A:
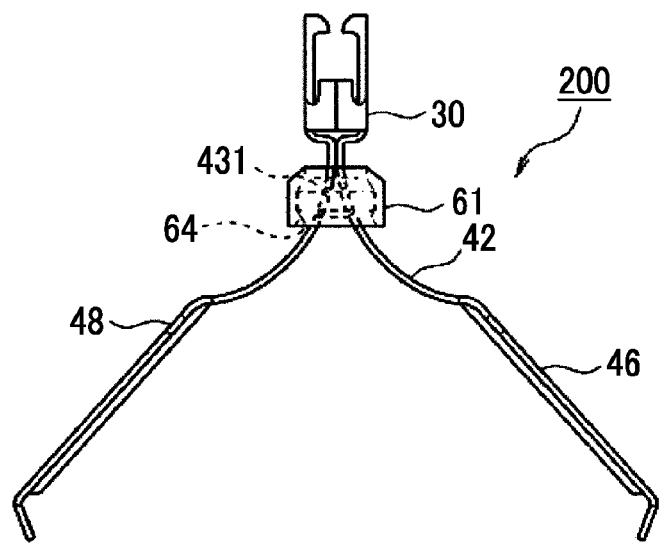
FIG. 23A is a view for describing a change in a clip state, and is a view illustrating a state where the clip is opened.
Figure 23B:
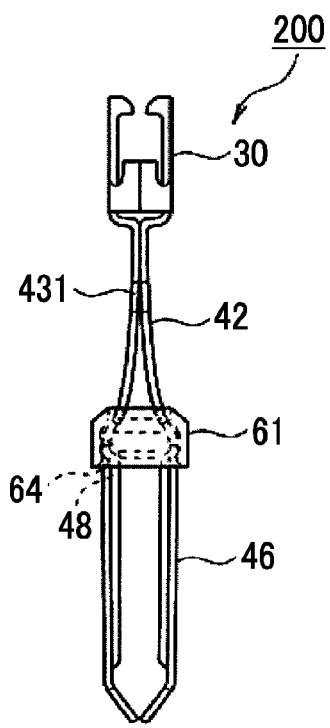
FIG. 23B is a view for describing a change in the clip state, and is a view illustrating a state where the clip is closed.
Figure 24:
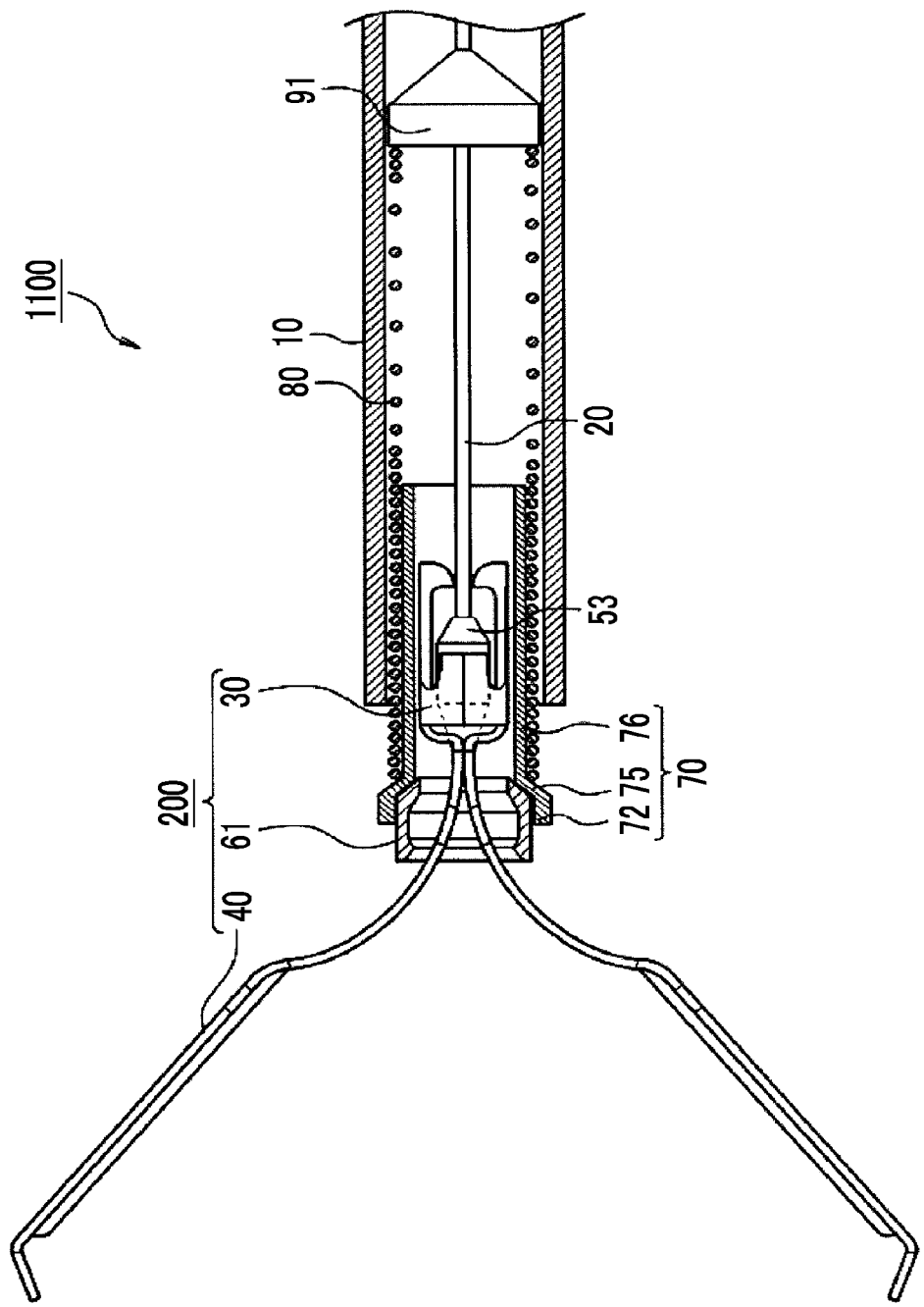
FIG. 24 is an enlarged view for describing an end portion region on a distal side of the endoscopic treatment instrument illustrated in FIG. 20.

FIGS. 21A and 21B are views for describing a state where the clamping member 61 is removed from the clip 200. FIG. 21A is a front view, and FIG. 21B is a side view. FIG. 22A is a view for describing the clip 200 having the clamping member 61 mounted thereon. FIG. 22A is a perspective view when the clip 200 is viewed from the proximal side. FIG. 22B is a sectional view of the clamping member 61. FIGS. 23A and 23B are views for describing a change in the state of the clip 200, FIG. 23A is a view illustrating a state where the clip 200 is opened, and FIG. 23B is a view illustrating a state where the clip 200 is closed. FIG. 24 is an enlarged view for describing an end portion region surrounded by a broken line on the distal side of the endoscopic treatment instrument 1100 illustrated in FIG. 20.

The clip 200 includes the first locking portion 30, a plurality of the arm 40, the clamping member 61, and a plurality of the distal claws 49 as main components.

In the clip 200 of the present embodiment, the first locking portion 30, the arm 40, and the distal claw 49 except for the clamping member 61 are formed as a single member, and all of these are seamlessly connected to each other.

The first locking portion 30 is a tubular body formed to be capable of engaging with the second locking portion 53 disposed on the distal side of the operation wire 20 of the endoscopic treatment instrument 1100.

For example, the first locking portion 30 can be formed by cutting a developed body of a tubular body from a metal plate having an appropriate thickness and bending the body in the circumferential direction. At the time of cutting, the plurality of arms 40 and distal claws 49 are integrally cut out from the metal plate. In this manner, the clip 200 integrally formed from one material can be easily formed.

As the metal material configuring the metal plate, it is possible to use stainless steel, titanium, or a titanium alloy. However, the metal material is not limited thereto. In addition, the above-described metal material may be appropriately subjected to corrosion-resistant coating treatment.

As illustrated in FIGS. 21A and 21B, the first locking portion 30 has a cutout in a portion on the side surface, and is elastically deformed by being pushed against the second locking portion 53. The cutout is widely opened, and the second locking portion 53 is inserted into the cutout in a widely opened state. If the second locking portion 53 is inserted, a load decreases, and the first locking portion 30 is restored to its original shape, thereby engaging with the second locking portion 53.

In addition, the engagement between the first locking portion 30 and the second locking portion 53 can be disengaged by causing the operation wire 20 to move forward and backward. Accordingly the clip 200 is separated by performing the treatment using the endoscope, thereby enabling the clip 200 to indwell the body lumen. The disengagement between the first locking portion 30 and the second locking portion 53 will be described in detail later.

The plurality of arms 40 are disposed on the distal side from the first locking portion 30, and are formed so as to face each other. The clip 200 according to the present embodiment has two arms 40 (arm 40a and arm 40b) as illustrated in FIG. 21A. However, the present invention may be embodied in an aspect having three arms or more.

The arm 40 has the bending portion 42, the linear portion 46, and the reinforcement portion 47.

The bending portion 42 is formed between the first locking portion 30 and the linear portion 46, and is bent outward.

The linear portion 46 is linearly formed on the distal side from the bending portion 42.

The reinforcement portion 47 is formed thicker than other portions of the bending portion 42 across the bending portion 42 and the linear portion 46. More specifically, the reinforcement portion 47 is subjected to an embossing process from the outside toward the inside of the linear portion 46, and the reinforcement portion 47 recessed by the embossing process extends from the linear portion 46 up to the bending portion 42.

The arm 40 is bent inward at the boundary between the linear portion 46 and the bending portion 42, and the reinforcement portion 47 reinforces this boundary portion. This boundary portion is one of locations to which the load is applied the most when the clip 200 is clamped. The reinforcement portion 47 can effectively prevent the arm 40 from being damaged.

The bending portion 42 is bent outward so that the curvature radius of the proximal side is larger than the curvature radius of the distal side. More specifically, the curvature radius of the bending portion 42 is formed in multiple stages, and is constant at each stage.

In this way, since the curvature radius is formed constant at each stage, fluctuations in the operation load when the clamping member is displaced with respect to the bending portion are constant at each stage. Therefore, the clip 200 according to the present embodiment can realize smooth operability.

In addition, since the present embodiment adopts this configuration, when the clip 200 is manufactured, it is easy to keep a bending condition of the bending portion 42 within a desired degree, and the yield of the clip 200 is improved.

In a case where the bending portion 42 described above is classified into three stages such as the proximal portion 43 formed on the proximal side of the bending portion 42, the distal portion 45 formed on the distal side from the proximal portion 43, the switching portion 44 formed at a location switching from the proximal portion 43 to the distal portion 45, the bending portion 42 has the following characteristics.

(i) The proximal portion 43 is formed using a first curvature radius $R_3$, the distal portion 45 is formed using a second curvature radius $R_5$, and the second curvature radius $R5$ is smaller than the first curvature radius $R_3$.

(ii) The length of the switching portion 44 in the longitudinal direction of the bending portion 42 is smaller than the thickness in the axial direction of the clamping member 61.

(iii) The switching portion 44 is formed using a third curvature radius $R_4$, the third the curvature radius $R_4$ is smaller than the first the curvature radius $R3$, and larger than the second curvature radius $R_5$.

A specific range of the proximal portion 43, the switching portion 44, and the distal portion 45 is illustrated in FIG. 21A for reference. In addition, an example has been described in which the bending portion 42 according to the present embodiment is classified into the three stages such as the proximal portion 43, the switching portion 44, and the distal portion 45. However, the bending portion 42 may be classified into two stages, or may be classified into four stages or more.

As described above, in the clip 200 according to the present embodiment, the switching portion 44 serving as a switching location from the proximal portion 43 to the distal portion 45 which respectively have different curvature radii is formed smaller than the thickness in the axial direction of the clamping member 61. Accordingly, the switching portion 44 is unlikely to interfere with the displacement of the clamping member 61 (operation of the endoscopic treatment instrument 1100). In addition, the curvature radius gradually decreases in the order of the proximal portion 43, the switching portion 44, and the distal portion 45. Therefore, it is possible to realize smooth operability in the procedures of the endoscopic treatment instrument 1100 having the clip 200 mounted thereon.

In addition, the bending portion 42 is terminated so as to be in contact with the axial direction of the first locking portion 30 toward the first locking portion 30 (locking portion). Thereafter, the bending portion 42 is bent at a right angle, and is connected to the first locking portion 30.

Here, "in contact with the axial direction" means a state where the bending portion 42 or the extension portion of the bending portion 42 is in contact with the axis of the first locking portion 30 which is a cylindrical body or the extension line of the axis.

In addition, "bent at a right angle" means bending outward as illustrated in FIG. 21A. More specifically, the term means bending in a direction toward the circumferential surface of the first locking portion 30 which is the cylindrical body.

An aspect in which the bending portion 42 is connected to the first locking portion 30 is not limited to an aspect in which the first locking portion 30 and the bending portion 42 are formed as a single member as in the present embodiment, and in which two of these are seamlessly connected to each other. For example, the present invention may be embodied as an aspect in which the first locking portion 30 and the bending portion 42 which are formed of different members are joined to each other by means of welding or adhesion.

Since both of these are formed as described above, the curvature radius (first curvature radius $R_3$) of the proximal side (proximal portion 43) of the bending portion 42 can be increased. Therefore, it is possible to reduce an operation load in a state where the clamping member 61 starts to be displaced (when the operation of the endoscopic treatment instrument 1100 starts).

Here, in the present embodiment, the axial direction of the first locking portion 30 is equal to the axial direction of the clip 200, and is substantially equal to the forward/backward movement direction of the operation wire 20.

The width and the length of the bending portion 42 increase toward the distal side. More specifically, as illustrated in FIG. 21B, the second diameter enlargement portion 451 which is gradually widened toward the distal side is formed on the distal side (distal portion 45) of the bending portion 42.

Since the present embodiment has this configuration, in a case where the clamping member 61 is displaced from the proximal side to the distal side of the arm 40, and when the clamping member 61 is located in the bending portion 42, the operation load becomes stronger in a stepwise manner (less likely to be gradually displaced). Therefore, based on the operation load, an operator of the endoscopic treatment instrument 1100 can recognize a progressing degree of the clamping member 61.

As illustrated in FIG. 21A, the arm 40 according to the present embodiment is bent in the middle of the second diameter enlargement portion 451. That is, the second diameter enlargement portion 451 is a portion switching from the bending portion 42 to the linear portion 46.

As illustrated in FIG. 21B, the bending portion 42 has the first diameter enlargement portion 431 which is wider than other portions of the bending portion 42 on the proximal side (proximal portion 43) of the bending portion 42. In addition, the projection 64 extends in the circumferential direction on the inner peripheral surface in the vicinity of the distal side opening 62 of the clamping member 61.

Since the present embodiment has this configuration, as illustrated in FIG. 23A, the projection 64 engages with the first diameter enlargement portion 431, and the clamping member 61 can be restrained from being separated from the proximal side of the clip 200.

As described above, the arm 40 is bent inward at the boundary between the linear portion 46 linearly formed on the distal side from the bending portion 42 and the bending portion 42. In addition, as illustrated in FIG. 21B, the recess 48 recessed in the width direction than other portions of the linear portion 46 is formed on the proximal side of the linear portion 46. In a state where the plurality of arms 40 are closed, the clamping member 61 can be fitted to the recess 48. More specifically, as illustrated in FIG. 23B, the projection 64 is fitted to the recess 48, thereby enabling the clip 200 to be maintained in a closed state.

Since the present embodiment has this configuration, in a case where the clamping member 61 is displaced from the proximal side of the arm 40 to the distal side, if the clamping member 61 is located in the linear portion 46, the operation load suddenly becomes weaker. Accordingly, the clamping member 61 is immediately fit to the recess 48, and the clip 200 is locked. Therefore, based on the operation load, the operator of the endoscopic treatment instrument 1100 can recognize the locked timing of the clip 200.

The plurality of distal claws 49 are formed in the distal end of the clip 200 and protrude inward. The plurality of distal claws 49 are formed so that one distal claw (distal claw 49a) engages with the other distal claw (distal claw 49b) in a state where the plurality of arms 40 are closed. In addition, the distal claw 49a is bifurcated, and the distal claw 49b engages with a portion therebetween. In this manner, the clip 200 can ligate the living body tissue.

The plurality of arms 40 are inserted into the inner diameter side of the clamping member 61. Although the clamping member 61 according to the present embodiment is formed in a circular shape, this configuration shows one of embodiments according to the present invention. That is, a member corresponding to the clamping member according to the present invention may have a space in which the plurality of arms can be inserted into the inner diameter side of the clamping member. For example, other shapes such as a rectangular shape and a polygonal shape may be employed.

The clamping member 61 has the distal side opening 62 and the proximal side opening 66.

The projection 64 extends in the circumferential direction on the inner circumferential surface of the clamping member 61 disposed in the vicinity of the distal side opening 62. As described above, the projection 64 is a portion which engages with the recess 48 in a state where the clip 200 is closed.

Although the projection 64 according to the present embodiment extends over the entire circumference of the inner circumferential surface, this configuration is an example. For example, the present invention may adopt an aspect in which the projection 64 is disposed in a portion of the inner circumferential surface.

In addition, the inclined portion 68 extends in the entire circumferential direction on the outer peripheral surface of the clamping member 61 disposed in the vicinity of the proximal side opening 66. The inclined portion 68 is inclined at an angle which enables the inclined portion 68 to come into contact with the step portion 75 of the diameter reduction sleeve 70. In the clip 200 according to the present embodiment, the diameter reduction sleeve 70 is also moved to the distal side as the drive unit 510 is moved relative to the distal side. In this case, the clamping member 61 is pushed to the distal side by the step portion 75. Accordingly, the clamping member 61 is moved relative to the distal side.

Details of the diameter reduction sleeve 70 will be described later.

Although the inclined portion 68 according to the present embodiment extends over the entire circumference of the outer peripheral surface, this configuration is an example. In addition, the inclined portion 68 has an inclined surface, but the inclined portion 68 is not limited to this shape. That is, a configuration may be adopted in which when the diameter reduction sleeve 70 is moved relative to the distal side, the diameter reduction sleeve 70 and the clamping member 61 can come into contact with each other so that the diameter reduction sleeve 70 can push the clamping member 61, and mutual shapes thereof are not limited to the above-described configuration.

<Details of Endoscopic Treatment Instrument 1100>

Next, the endoscopic treatment instrument 1100 will be described in detail with reference to FIG. 24 or FIGS. 25A, 25B, and 25C.

Figure 25A:
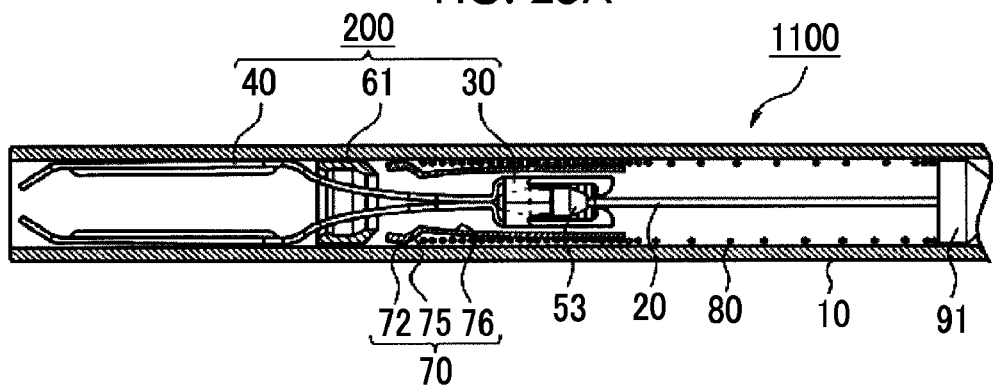
FIG. 25A is a view for describing a gripping operation of the endoscopic treatment instrument on which the clip is mounted, and illustrates a state the mounted clip is accommodated inside the sheath.
Figure 25B:
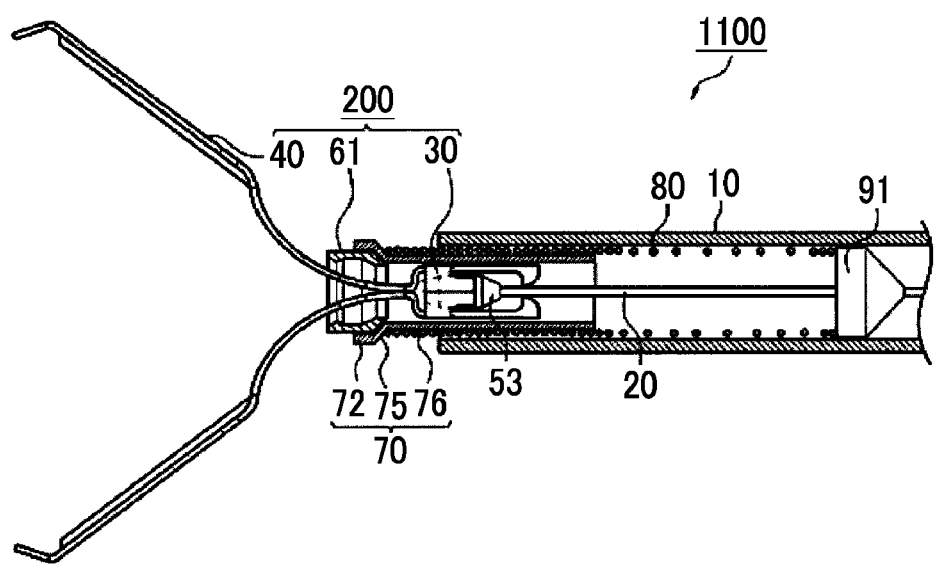
FIG. 25B is a view for describing a gripping operation of the endoscopic treatment instrument on which the clip is mounted, and illustrates a state the clip is protruded from a distal side of the sheath and arms are widely opened.
Figure 25C:
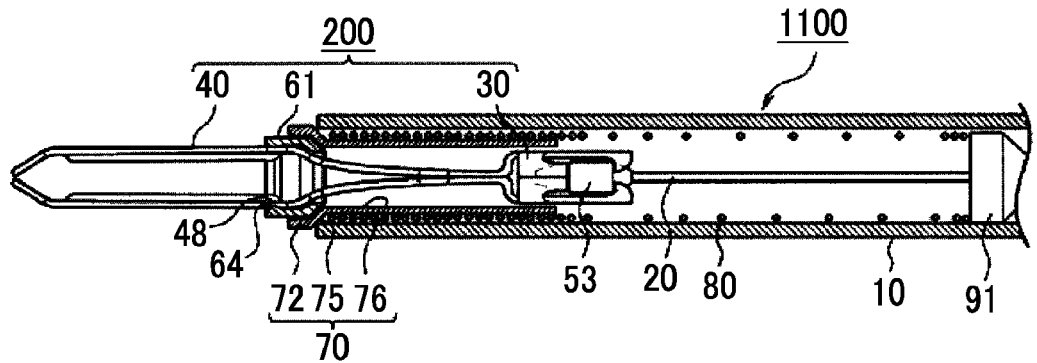
FIG. 25C is a view for describing a gripping operation of the endoscopic treatment instrument on which the clip is mounted, and illustrates a state the clip is closed.

FIG. 24 is an enlarged view for describing an end portion region on the distal side illustrated by a broken circle on the distal side of the endoscopic treatment instrument 1100 illustrated in FIG. 20. FIGS. 25A, 25B, and 25C are views for describing a gripping operation of the endoscopic treatment instrument 1100 having the clip 200 mounted thereon. FIG. 25A illustrates a state where the mounted clip 200 is accommodated inside the sheath 10, FIG. 25B illustrates a state where the clip 200 protrudes from the distal side of the sheath 10 so as to open the arm 40, and FIG. 25C illustrates a state where the clip 200 is closed.

FIG. 24 illustrates a cross section of the sheath 10, the clamping member 61, the diameter reduction sleeve 70, and the elastic portion 80. Other configurations are illustrated using a side view, the endoscopic treatment instrument 1100 having the clip 200 mounted thereon is schematically illustrated therein. In addition, FIGS. 25A, 25B, and 25C (to be described later) schematically illustrate the present invention in the same manner using the sectional view and the side view together.

As illustrated in FIG. 24, the endoscopic treatment instrument 1100 can be used with the clip 200 mounted thereon.

The endoscopic treatment instrument 1100 includes the elongated sheath 10, the operation wire 20 inserted into the sheath 10 so as to be movable forward and backward, and the second locking portion 53 which engages with the first locking portion 30 in the clip 200.

The elongated sheath 10 is a long and flexible tubular member. For example, the sheath 10 can be configured to comprise a coil layer (not illustrated) around which a metal wire is wound long. An inner layer (not illustrated) made of fluorine-based polymer may configure the inner peripheral surface of the coil layer. Alternatively, the sheath 10 may be configured to comprise a flexible resin member instead of the metal member. Alternatively, the sheath 10 may be formed in a tubular shape by using the flexible resin member.

The inner diameter of the sheath 10 has a size in which at least the operation wire 20 is slidable. The inner diameter of the sheath 10 may secure a size in which the clip 200 can be accommodated. In the present embodiment, the clip 200 including the arms 40 in a closed state can be accommodated inside the sheath 10 (refer to FIG. 25A). Specifically, the inner diameter of the sheath 10 is 100 μm to 2.4 mm, for example. In addition, the thickness of the sheath 10 is 100 μm to 350 μm, for example. In this manner, it is possible to improve the flexibility of the sheath 10.

The operation wire 20 is inserted into the sheath 10 so as to be movable forward and backward in the axial direction. For example, the operation wire 20 is made of a highly rigid metal material such as stainless steel, corrosion-resistant coated steel wire, and titanium or titanium alloys.

The second locking portion 53 is disposed continuous with the distal side of the operation wire 20. The second locking portion 53 can engage with the first locking portion 30 disposed in the clip 200. FIG. 24 illustrates a state where the first locking portion 30 and the second locking portion 53 engage with each other.

In the present embodiment, although a shape of the second locking portion 53 is formed in a knob shape, this shape is an example. That is, the shape of the second locking portion 53 can be changed depending on a method of fitting the second locking portion 53 to the first locking portion 30, and the configuration is not limited to the above-described shape.

The diameter reduction sleeve 70 has the diameter enlargement portion 72 disposed on the distal side, the sleeve body 76 disposed on the proximal side, and the step portion 75 located between the diameter enlargement portion 72 and the sleeve body 76. In the diameter reduction sleeve 70, at least the diameter enlargement portion 72 decreases in diameter due to an external force, thereby enabling the diameter reduction sleeve 70 to be accommodated in the distal side of the sheath 10 (refer to FIG. 25A).

The diameter reduction sleeve 70 is inserted into the sheath 10 so as to be movable forward and backward. The elastic portion 80 which can slide inside the sheath 10 so as to be movable forward and backward and which can extend in the axial direction is connected to the diameter reduction sleeve 70. More specifically, the elastic portion 80 is welded to the diameter reduction sleeve 70 in the center portion in the axial direction, and both of these cannot be separated from each other.

The step portion 75 according to the present embodiment is formed in a tapered shape between the sleeve body 76 and the diameter enlargement portion 72. An external force is applied to the diameter reduction sleeve 70 so as to decreases the diameter of the diameter enlargement portion 72 and the step portion 75. In this manner, the diameter reduction sleeve 70 is allowed to move into the sheath 10.

The configuration material of the diameter reduction sleeve 70 is not limited to a specific material as long as the diameter of the member can be decreased by the external force. For example, the configuration material may be metal, resin, or an elastomer such as rubber. In view of strength requirements, it is preferable that the diameter enlargement portion 72 is made of metal such as stainless steel. For example, one or more slits (not illustrated) cut out from the distal side end portion to the proximal side of the diameter enlargement portion 72 may be formed so that the diameter of the diameter enlargement portion 72 is likely to be decreased by the external force. For example, the above-described slit may be continuously formed from the distal side end portion of the diameter enlargement portion 72 to at least the intermediate region of the step portion 75.

When the diameter reduction sleeve 70 protrudes from the distal side of the sheath 10, the diameter of the diameter enlargement portion 72 increases, and the step portion 75 can come into contact with the distal end of the sheath 10 (refer to FIG. 25B).

In this manner, the diameter reduction sleeve 70 can be regulated in moving into the sheath 10 again. In a case where the diameter reduction sleeve 70 needs to be accommodated again in the above-described state, the diameter of the diameter enlargement portion 72 and the step portion 75 is decreased by the external force.

The proximal side end portion of the elastic portion 80 is connected to the centering member 91. The operation wire 20 is inserted into and fixed to substantially the center of the centering member 91. Therefore, in conjunction with the operation of the operation wire 20 in the forward/backward movement direction, the centering member 91 and the elastic portion 80 connected thereto are also operable in the forward/backward movement direction. Since the present embodiment is provided with the centering member 91, the insertion position of the operation wire 20 is regulated so as to follow the central axis in the distal side region of the sheath 10. That is, the operation wire 20 is located inside the sheath 10 at the center position of the sheath 10 in a cross section by the centering member 91. Since the operation wire 20 is located at the center position, the insertion path is corrected inside the sheath 10, and it is possible to realize a preferable operation scheduled based on the design.

The elastic portion 80 is configured to a member which can extend in the axial direction. For example, the elastic portion 80 may be made of metal, resin, or an elastomer such as rubber. In view of strength requirements, it is preferable that the elastic portion 80 is a coil around which a fine stainless steel or tungsten wire is wound, for example. A winding method of the above-described coil is not particularly limited, and may employ equal pitches, variable pitches, or a combination thereof. In a natural state of the elastic portion 80 which is the coil according to the present embodiment, the distal side region and the proximal side region are closely wound, and the intermediate region is wound at equal pitches. The above-described coil may be a coil spring.

<Ligation Using Clip 200>

Next, ligation using the clip 200 will be described with reference to FIGS. 25A, 25B, and 25C.

FIGS. 25A, 25B, and 25C are views for describing a gripping operation of the endoscopic treatment instrument 1100 having the clip 200 mounted thereon. FIG. 25A illustrates a state where the mounted clip 200 is accommodated inside the sheath 10. FIG. 25B illustrates a state where the clip 200 protrudes from the distal side of the sheath 10 so as to open the arm 40. FIG. 25C illustrates a state where the clip 200 is closed.

The clip 200 mounted on the endoscopic treatment instrument 1100 is accommodated in the sheath 10 as described above (refer to FIG. 25A). In this state, the endoscopic treatment instrument 1100 is inserted into the body lumen inside the body.

If the distal side end portion of the sheath 10 reaches the vicinity of the living body tissue requiring ligation, the operation wire 20 is first pushed to the distal side. The clip 200 and the clamping member 61 protrude from the distal end of the sheath 10. The clip 200 is naturally spread out to the maximum opening width by the self-openable force (not illustrated).

Furthermore, the operation wire 20 is pushed to the distal side, thereby causing the diameter reduction sleeve 70 to protrude from the distal end of the sheath 10 and causing the diameter of the diameter enlargement portion 72 and the step portion 75 to increase to the original diameter. The clamping member 61 is fitted into the diameter enlargement portion 72 (refer to FIG. 25B).

In a case where the operation wire 20 is pushed to the distal side, as illustrated in FIG. 25B, the distal end surface of the second locking portion 53 comes into contact with the joint between the arm 40 (bending portion 42) and the first locking portion 30, that is, the bent portion on the proximal side of the bending portion 42. Then, the distal end surface pushes the bending portion, thereby pushing the clip 200 to the distal side together with the operation wire 20.

Next, the clip 200 is positioned with respect to the ligation site, and the operation wire 20 is drawn to the proximal side in a state where the distal claw 49 of the clip 200 is pushed against the ligation site.

In a case where the operation wire 20 is drawn to the proximal side, the second locking portion 53 engages with the first locking portion 30. Accordingly, the clip 200 is drawn to the proximal side together with the operation wire 20.

The clamping member 61 comes into contact with the inner surface of the step portion 75, and is fitted into the diameter enlargement portion 72. Accordingly, the clamping member 61 is regulated in further moving to the proximal side relative to the diameter reduction sleeve 70. Therefore, even if the clip 200 is drawn to the proximal side, the clamping member 61 is not drawn into the sheath 10 after passing through the inner diameter of the diameter reduction sleeve 70. In addition, the clamping member 61 is fitted to the diameter enlargement portion 72. Accordingly, a decrease in the distal end diameter of the diameter reduction sleeve 70 which is caused by the external force is restrained. Even if the operation wire 20 is drawn to the proximal side with a strong force, the diameter reduction sleeve 70 is not drawn into the sheath 10.

The operation wire 20 and the diameter reduction sleeve 70 are connected to each other by the elastic portion 80. Therefore, even after the diameter reduction sleeve 70 is regulated in moving to the proximal side relative to the endoscopic treatment instrument 1100, the operation wire 20 is further drawn to the proximal side. In this manner, the elastic portion 80 extends, and the first locking portion 30 disposed in the distal end of the operation wire 20 is further drawn to the proximal side inside the sheath 10.

In this way, even after the diameter reduction sleeve 70 and the clamping member 61 are regulated in moving to the proximal side relative to the endoscopic treatment instrument 1100, if the operation wire 20 is drawn, the arm 40 is drawn into the clamping member 61 and closed, thereby causing the distal claw 49 to ligate the ligation site. However, the arm 40 can be widely opened by pushing the operation wire 20 again. Accordingly, it is possible to grip the ligation site again.

If the operation wire 20 is further drawn to the proximal side after the optimum ligation is confirmed, the clamping member 61 is fitted to the recess 48 disposed in the arm 40, thereby maintaining a closed state of the arm 40 (refer to FIG. 25C).

As illustrated in FIG. 25C, in a state where the clip 200 is regulated in moving to the proximal side relative to the endoscopic treatment instrument 1100, the operation wire 20 is further drawn to the proximal side. In this manner, the first locking portion 30 is deformed outward be receiving stress, thereby disengaging the second locking portion 53 and the first locking portion 30 from each other.

Through the above-described operations, the clip 200 is separated from the endoscopic treatment instrument 1100, and is caused to indwell the inside of the body.

As described above, the endoscopic treatment instrument 1100 according to the present embodiment allows the clip 200 to be mounted thereon, and can indwell the inside of the body without causing any damage. Accordingly, while the clip 200 is mounted thereon again, the endoscopic treatment instrument 1100 can repeat the ligation. In addition, the clip 200 indwelling the inside of the body after mounted on the endoscopic treatment instrument 1100 is not cut or damaged when the clip 200 is separated from the endoscopic treatment instrument 1100. Therefore, a cutting piece is generated, and there is no possibility that a damaged site may cause damage to the inside of the body.

Hitherto, the embodiments according to the present invention have been described. The clip 200 which can be mounted on the endoscopic treatment instrument 1100 according to the present embodiment is appropriately used as a reference of one embodiment of the clip according to the present invention.

The present invention is not limited to the above-described embodiments, but includes various modifications and improvements as long as the object of the present, invention is achieved.

The above embodiment encompasses the following technical concept.

(1) There is an endoscopic clip device including a clip that comprises a plurality of arms for gripping a living body tissue and a locking portion disposed on a proximal side of the arms, and a treatment instrument body that comprises an elongated sheath, and an operation wire which is inserted into the sheath so as to be movable forward and backward, and in which a chunky distal connection portion is disposed in a distal end. The locking portion of the clip comprises an accommodation portion which internally has a space for accommodating the distal connection portion, and a protruding portion which is formed to protrude inward on a proximal side of the accommodation portion. The distal connection portion is pushed against the protruding portion from the proximal side so that the protruding portion is elastically deformed outward, the accommodation portion is opened so that the distal connection portion can be accommodated in a forward/backward movement direction of the operation wire, and the distal connection portion passes through the protruding portion on a distal side in the forward/backward movement direction so that the protruding portion is elastically restored inward. In a state where the distal connection portion is accommodated in the accommodation portion, the distal connection portion draws the operation wire to the proximal side in the forward/backward movement direction so that the arms are closed to grip the living body tissue, the distal connection portion further draws the operation wire to the proximal side so that the distal connection portion causes the protruding portion to be deformed outward and the accommodation portion is opened, and the distal connection portion is drawable from the accommodation portion.

(2) In the endoscopic clip device according to (1) described above, a first inclined surface is disposed in a proximal portion of the distal connection portion, and a normal direction of the first inclined surface is an obliquely outward orientation toward the proximal side. In a state where the distal connection portion is accommodated in the accommodation portion, the distal connection portion draws the operation wire to the proximal side in the forward/backward movement direction so that the first inclined surface causes the protruding portion to be deformed outward.

(3) In the endoscopic clip device according to (1) or (2) described above, a second inclined surface is disposed in a distal portion of the distal connection portion, and the normal direction of the second inclined surface is an obliquely outward orientation toward the distal side. The distal connection portion is pushed against the protruding portion from the proximal side so that the second inclined surface causes the protruding portion to be elastically deformed outward.

(4) In the endoscopic clip device according to (2) or (3) described above, at least any one of the first inclined surface and the second inclined surface has a conical shape.

(5) In the endoscopic clip device according to any one of (1) to (4) described above, a cylindrical sleeve which can be accommodated inside the sheath and which accommodates the distal connection portion is disposed in the distal portion of the operation wire. At least a portion of an inner diameter of the sleeve is smaller than an outer diameter of the locking portion when the distal connection portion is drawable from the accommodation portion.

(6) In the endoscopic clip device according to (5) described above, the sleeve has a diameter enlargement portion which is disposed on the distal side and which is elastically self-openable, a diameter reduction step portion which is disposed on the proximal side of the diameter enlargement portion, and a cylindrical sleeve body which is disposed on the proximal side from the diameter reduction step portion and whose radial rigidity is higher than that of the diameter enlargement portion. The inner diameter of the sleeve body is smaller than the outer diameter of the locking portion when the distal connection portion is drawable from the accommodation portion.

(7) In the endoscopic clip device according to (5) or (6) described above, when the arms are closed to grip the living body tissue, the protruding portion is accommodated inside the sleeve, and the operation wire is further drawn to the proximal side so that the protruding portion protrudes to the proximal side from the sleeve, and the protruding portion is deformable outward until the distal connection portion is drawable from the accommodation portion.

(8) There is provided a clip used for the endoscopic clip device according to any one of (1) to (7). The clip includes a plurality of arms for gripping a living body tissue, and a locking portion that is disposed on a proximal side of the arms. The locking portion comprises a base which is connected to the proximal side of the arms, an accommodation portion which is configured to comprise a plurality of projection pieces formed to project to the proximal side from the base and which internally has a space, and protruding portions respectively formed to protrude inward in a distal portion on the proximal side of the projection pieces.

(9) In the clip according to (8) described above, the base has an annular shape formed by bending a plate material and causing edges of the plate material to abut on each other. The plurality of projection pieces are arranged apart from each other around the base having an annular shape. A joint of the edges abutting on each other is disposed at an intermediate position between the projection pieces adjacent to each other.

(10) In the clip according to (8) or (9) described above, a plurality of recesses recessed toward the distal side are formed in a peripheral edge on the proximal side of the base. The projection pieces are respectively formed to project to the proximal side from a bottom of the recesses.

(11) In the clip according to (10) described above, the joint of the edges is disposed at a position where the recesses are not formed in the base.

(12) there is provided an endoscopic clip device including a clip that comprises a plurality of arms for gripping a living body tissue, and a locking portion disposed on a proximal side of the arms, and a treatment instrument body that comprises an elongated sheath, and an operation wire which is inserted into the sheath so as to be movable forward and backward, and in which a distal connection portion is disposed in a distal end. The locking portion and the distal connection portion are locked and connected to each other around an axis of the operation wire. A cylindrical sleeve which accommodates the distal connection portion is disposed in the distal portion of the operation wire. The operation wire is rotated to generate torques so that the locking portion, the distal connection portion, and the sleeve are axially rotated around the axis inside the sheath.

(13) In the endoscopic clip device according to (12) described above, the locking portion comprises a base which is connected to the proximal end of the arms, and a projection piece which is formed to project to the proximal side and which has at least a flat inner surface side. A planar portion is formed around the distal connection portion. In a state where surfaces of the projection piece and the planar portion are aligned with each other, the distal connection portion is connected to the locking portion.

(14) In the endoscopic clip device according to (13) described above, in the locking portion, the N-number (N is an integer equal to or greater than 2) of the projection pieces are arranged facing each other and apart from each other around the base. The N-integer multiple number of the planar portions are formed in the distal connection portion, and in a state where surfaces of the plurality of projection pieces are respectively aligned with surfaces of the planar portions, the distal connection portion is connected to the locking portion.

(15) In the endoscopic clip device according to any one of (12) to (14) described above, the periphery of the distal connection portion is formed in a prismatic shape which is a rotationally symmetric shape.

(16) In the endoscopic clip device according to any one of (13) to (15) described above, the locking portion of the clip comprises an accommodation portion which internally has a space for accommodating the distal connection portion and which is configured to comprise the plurality of projection pieces, and a protruding portion which is formed to protrude inward in the proximal portion of the projection pieces.

(17) In the endoscopic clip device according to (16) described above, the distal connection portion has a chunky shape having a large diameter body and a neck portion whose diameter is smaller than that of the large diameter body. The protruding portion is fitted to the neck portion of the distal connection portion accommodated in the accommodation portion so that the distal connection portion is connected to the locking portion.

(18) In the endoscopic clip device according to (17) described above, a planar portion is formed around the neck portion. In a state where a distal edge of the protruding portion is in contact with the planar portion, the distal connection portion is connected to the locking portion.

(19) In the endoscopic clip device according to any one of (12) to (18) described above, the distal portion of the distal connection portion has a flat inclined surface whose diameter is reduced toward the distal side. In a state where a surface of the arms of the clip and the inclined surface are aligned with each other, the distal connection portion is connected to the locking portion.

(20) There is provided a clip used for an endoscopic treatment instrument comprising an elongated sheath and an operation wire inserted into the sheath so as to be movable forward and backward. The clip includes a locking portion that engages with a distal side of the operation wire, a plurality of arms that are disposed on the distal side from the locking portion, and that are opened outward using a self-openable force, a clamping member into which the plurality of arms are inserted, and whose position relative to the plurality of arms is displaced from the proximal side to the distal side so that the plurality of arms are closed inward, A plurality of claws that are disposed on the distal side from the plurality of arms, and that protrude inward. Each of the arms comprises a bending portion which is bent outward so that a curvature radius on the proximal side is larger than a curvature radius on the distal side.

(21) In the clip according to (20) described above, the curvature radius of the bending portion is formed in multiple stages and is constant at each stage.

(22) In the clip according to (20) or (21) described above, the bending portion comprises a proximal portion which is formed on a proximal side of the bending portion so as to have a first curvature radius, a distal portion which is formed on a distal side from the proximal side so as to have a second curvature radius smaller than the first curvature radius, and a switching portion which is formed in a location where the proximal portion is switched to the distal portion. A length of the switching portion in a longitudinal direction of the bending portion is smaller than a thickness in an axial direction of the clamping member.

(23) In the clip according to (22) described above, the switching portion is formed so as to have a third curvature radius. The third curvature radius is smaller than the first curvature radius, and is larger than the second curvature radius.

(24) In the clip according to any one of (20) to (23) described above, the arm comprise a linear portion which is linearly formed on the distal side from the bending portion, and a reinforcement portion which is formed across the bending portion and the linear portion so as to be thicker than other portions of the bending portion. The arm is bent inward at a boundary between the linear portion and the bending portion.

(25) In the clip according to any one of (20) to (24) described above, the bending portion is connected to the locking portion by being bent at a right angle after the bending portion is terminated so as to come into contact with the locking portion in the axial direction of the locking portion.

(26) In the clip according to any one of (20) to (25) described above, a width length of the bending portion increases toward the distal side.

(27) In the clip according to (26) described above, the arm is bent inward at a boundary between the linear portion linearly formed on the distal side from the bending portion and the bending portion. A recess which is further recessed in a width direction compared to other portions of the linear portion is formed on the proximal side of the linear portion. In a state where the plurality of arms are closed, the clamping member can be fitted to the recess.

(28) There is proved an endoscopic treatment instrument comprising the clip according to any one of (20) to (27) described above. The endoscopic treatment instrument includes an elongated sheath, and an operation wire that is inserted into the sheath so as to be movable forward and backward. The clip is mounted on the distal side of the operation wire.

REFERENCE SIGNS LIST

10 SHEATH
20 OPERATION WIRE
30 FIRST LOCKING PORTION
40, 40a, 40b ARM
42 BENDING PORTION
43 PROXIMAL PORTION
44 SWITCHING PORTION
45 DISTAL PORTION
46 LINEAR PORTION
47 REINFORCEMENT PORTION
48 RECESS
49, 49a, 49b DISTAL CLAW
50 DISTAL CONNECTION PORTION
51 NECK PORTION
52 FIRST INCLINED SURFACE
53 SECOND LOCKING PORTION
54 SECOND INCLINED SURFACE
56 STRUT
57 FLANGE

60 CENTERING PORTION
61 CLAMPING MEMBER
62 DISTAL SIDE OPENING
64 PROJECTION
66 PROXIMAL SIDE OPENING
68 INCLINED PORTION
70 DIAMETER REDUCTION SLEEVE
72 DIAMETER ENLARGEMENT PORTION
74 DIAMETER REDUCTION STEP PORTION
75 STEP PORTION
76 SLEEVE BODY
80 ELASTIC PORTION
82 STATIONARY WIRE
84 MOVABLE WIRE
90 TREATMENT INSTRUMENT BODY
91 CENTERING MEMBER
92 FINGER RING
94 SLIDER
96 MAIN BODY SHAFT
100 ENDOSCOPIC CLIP DEVICE (CLIP DEVICE)
110 CLIP
120 ARM
121 WIDENED PORTION
122 PROXIMAL PORTION
123 NARROW WIDTH PORTION
124 ARM BODY
125 REINFORCEMENT PORTION
126 CLAW
130 LOCKING PORTION
132 SPACE
134 ACCOMMODATION PORTION
136 BASE
137 RECESS
138 EDGE
139 BOTTOM
140 PROTRUDING PORTION
142 PROJECTION PIECE
150 CLAMPING MEMBER
200 CLIP
431 FIRST DIAMETER ENLARGEMENT PORTION
451 SECOND DIAMETER ENLARGEMENT PORTION
500 FINGER RING
510 DRIVE UNIT
520 OPERATION UNIT BODY
1100 ENDOSCOPIC TREATMENT INSTRUMENT

The invention claimed is:

1. An endoscopic clip device, comprising:
a clip comprising a plurality of arms configured to grip a living body tissue and a locking portion positioned on a proximal side of the arms;
a treatment instrument body comprising an elongated sheath, an operation wire which is inserted into the elongated sheath such that the operation wire is movable forward and backward, and a distal connection portion positioned in a distal end of the operation wire; and
a sleeve configured to be accommodated inside the elongated sheath and accommodating the distal connection portion in a distal portion of the operation wire such that at least a portion of an inner diameter of the sleeve is smaller than an outer diameter of the locking portion when the distal connection portion is drawable from the accommodation portion,
wherein the locking portion of the clip comprises an accommodation portion which internally has a space that accommodates the distal connection portion, and a protruding portion which is formed to protrude inward on a proximal side of the accommodation portion, the distal connection portion is pushed against the protruding portion from the proximal side such that the protruding portion is elastically deformed outward, the accommodation portion is opened such that the distal connection portion is accommodated in a forward/backward movement direction of the operation wire, and the distal connection portion passes through the protruding portion on a distal side in the forward/backward movement direction such that the protruding portion is elastically restored inward, and in a state where the distal connection portion is accommodated in the accommodation portion, the distal connection portion draws the operation wire to the proximal side in the forward/backward movement direction such that the arms are closed to grip the living body tissue, the distal connection portion further draws the operation wire to the proximal side such that the distal connection portion causes the protruding portion to be deformed outward and the accommodation portion is opened, the distal connection portion is drawable from the accommodation portion, the sleeve has a diameter enlargement portion which is positioned on the distal side and which is elastically self-openable, a diameter reduction step portion which is positioned on a proximal side of the diameter enlargement portion, and a cylindrical sleeve body which is positioned on the proximal side of the diameter enlargement portion from the diameter reduction step portion and whose radial rigidity is higher than radial rigidity of the diameter enlargement portion, and the inner diameter of the cylindrical sleeve body is smaller than the outer diameter of the locking portion when the distal connection portion is drawable from the accommodation portion.

2. The endoscopic clip device according to claim 1, wherein the distal connection portion has a first inclined surface formed in a proximal portion of the distal connection portion such that a normal direction of the first inclined surface is an obliquely outward orientation toward the proximal side, and in a state where the distal connection portion is accommodated in the accommodation portion, the distal connection portion draws the operation wire to the proximal side in the forward/backward movement direction such that the first inclined surface causes the protruding portion to be deformed outward.

3. The endoscopic clip device according to claim 2, wherein the distal connection portion has a second inclined surface formed in a distal portion of the distal connection portion such that the normal direction of the second inclined surface is an obliquely outward orientation toward the distal side, and the distal connection portion is pushed against the protruding portion from the proximal side such that the second inclined surface causes the protruding portion to be elastically deformed outward.

4. The endoscopic clip device according to claim 3, wherein at least one of the first inclined surface and the second inclined surface has a conical shape.

5. The endoscopic clip device according to claim 1, wherein when the arms are closed to grip the living body tissue, the protruding portion is accommodated inside the sleeve, and the operation wire is further drawn to the proximal side such that the protruding portion protrudes to the proximal side from the sleeve, and the protruding portion is deformable outward until the distal connection portion is drawable from the accommodation portion.

6. A clip for an endoscopic clip device, comprising:
a plurality of arms configured to grip a living body tissue; and
a locking portion positioned on a proximal side of the arms and comprising a base which is connected to the proximal side of the arms, an accommodation portion comprising a plurality of projection pieces formed to project to a proximal side of the locking portion from the base and internally having a space, and a plurality of protruding portions respectively formed to protrude inward on proximal side of the projection pieces, the base has an annular shape formed by bending a plate material and causing edges of the plate material to abut on each other, the plurality of projection pieces is positioned apart from each other around the base having an annular shape, and a joint of the edges abutting on each other is positioned at an intermediate position between the projection pieces adjacent to each other, the base has a plurality of recesses recessed toward a distal side of the base and formed in a peripheral edge on a proximal side of the base, and the projection pieces are respectively formed to project to the proximal side from a bottom of the recesses.

7. The clip according to claim 6, wherein the joint of the edges is positioned at a position where the recesses are not formed in the base.

8. An endoscopic clip device, comprising:
a clip comprising a plurality of arms configured to grip a living body tissue, and a locking portion positioned on a proximal side of the arms; and
a treatment instrument body comprising an elongated sheath, an operation wire which is inserted into the sheath such that the operation wire is movable forward and backward, and a distal connection portion positioned in a distal end of the operation wire; and
a sleeve configured to be accommodated in the elongated sheath and accommodating the distal connection portion in a distal portion of the operation wire such that at least a portion of an inner diameter of the sleeve is smaller than an outer diameter of the locking portion when the distal connection portion is drawable from the accommodation portion,
wherein the locking portion and the distal connection portion are locked and connected to each other around an axis of the operation wire, the operation wire is rotated to generate torques such that the locking portion, the distal connection portion, and the sleeve are axially rotated around the axis inside the sheath, the sleeve has a diameter enlargement portion which is positioned on the distal side and which is elastically self-openable, a diameter reduction step portion which is positioned on a proximal side of the diameter enlargement portion, and a cylindrical sleeve body which is positioned on the proximal side of the diameter enlargement portion from the diameter reduction step portion and whose radial rigidity is higher than radial rigidity of the diameter enlargement portion, and the inner diameter of the cylindrical sleeve body is smaller than the outer diameter of the locking portion when the distal connection portion is drawable from the accommodation portion.

9. The endoscopic clip device according to claim 8, wherein the locking portion comprises a base which is connected to a proximal end of the arms, and a projection piece which is formed to project to the proximal side and which has at least a flat inner surface side, a planar portion is formed around the distal connection portion, and in a state where surfaces of the projection piece and the planar portion are aligned with each other, the distal connection portion is connected to the locking portion.

10. The endoscopic clip device according to claim 9, wherein in the locking portion, the projection piece is formed in an N-number of projection pieces such that a plurality of projection pieces is positioned facing each other and apart from each other around the base, where N is an integer equal to or greater than 2, and the planar portion is formed in an N-integer multiple number of the such that a plurality of planar portions is formed in the distal connection portion, and in a state where surfaces of the plurality of projection pieces are respectively aligned with surfaces of the planar portions, the distal connection portion is connected to the locking portion.

11. The endoscopic clip device according to claim 10, wherein the periphery of the distal connection portion is formed in a prismatic shape which is a rotationally symmetric shape.

12. The endoscopic clip device according to claim 9, wherein the locking portion of the clip comprises an accommodation portion which internally has a space that accommodates the distal connection portion and which comprises the plurality of projection pieces, and a protruding portion which is formed to protrude inward in the proximal portion of the projection pieces.

13. The endoscopic clip device according to claim 12, wherein the distal connection portion has a chunky shape having a large diameter body and a neck portion whose diameter is smaller than a diameter of the large diameter body, and the protruding portion is fitted to the neck portion of the distal connection portion accommodated in the accommodation portion such that the distal connection portion is connected to the locking portion.

14. The endoscopic clip device according to claim 13, wherein the neck portion has a planar portion formed around the neck portion, and in a state where a distal edge of the protruding portion is in contact with the planar portion, the distal connection portion is connected to the locking portion.

15. The endoscopic clip device according to claim 8, wherein the distal portion of the distal connection portion has a flat inclined surface whose diameter is reduced toward the distal side, and in a state where a surface of the arms of the clip and the inclined surface are aligned with each other, the distal connection portion is connected to the locking portion.

16. A clip for an endoscopic treatment instrument, comprising:
a locking portion that engages with a distal side of an operation wire inserted into an elongated sheath of an endoscopic treatment instrument through a distal connection portion of the endoscopic treatment instrument such that the operation wire is movable forward and backward;
a plurality of arms positioned on a distal side of the locking portion on an opposite side with respect to the distal connection portion of the endoscopic treatment instrument and configured to open outward by a self-openable force; and
a clamping member into which the plurality of arms is inserted, and whose position relative to the plurality of arms is displaced from a proximal side of the arms to a distal side of the arms such that the clamping member closes a plurality of claws formed at the distal side of the plurality of arms inward,
wherein each of the arms comprises a bending portion which is bent outward such that a curvature radius on the proximal side of the arms is larger than a curvature radius on the distal side of the arms, the locking portion includes a base which is connected to the proximal side of the arms, an accommodation portion comprising a plurality of projection pieces formed to project to a proximal side of the locking portion from the base and internally having a space, and a plurality of protruding portions respectively formed to protrude inward on a proximal side of the projection pieces, the base has an annular shape formed by bending a plate material and causing edges of the plate material to abut on each other, the plurality of projection pieces is positioned apart from each other around the base having an annular shape, and a joint of the edges abutting on each other is positioned at an intermediate position between the projection pieces adjacent to each other, the base has a plurality of recesses recessed toward a distal side of the base and formed in a peripheral edge on a proximal side of the base, and the projection pieces are respectively formed to project to the proximal side from a bottom of the recesses.

17. The clip according to claim 16, wherein the curvature radius of the bending portion is formed in multiple stages and is constant at each of the multiple stages.

18. The clip according to claim 16, wherein the bending portion comprises a proximal portion which is formed on a proximal side of the bending portion so as to have a first curvature radius, a distal portion which is formed on a distal side of the bending portion so as to have a second curvature radius smaller than the first curvature radius, and a switching portion which is formed in a location where the proximal portion is switched to the distal portion, and a length of the switching portion in a longitudinal direction of the bending portion is smaller than a thickness in an axial direction of the clamping member.

19. The clip according to claim 18, wherein the switching portion is formed so as to have a third curvature radius, and the third curvature radius is smaller than the first curvature radius, and is larger than the second curvature radius.

20. The clip according to claim 16, wherein each of the arms comprises a linear portion which is linearly formed on the distal side from the bending portion, and a reinforcement portion which is formed across the bending portion and the linear portion so as to be thicker than other portions of the bending portion, and each of the arms is bent inward at a boundary between the linear portion and the bending portion.

21. The clip according to claim 16, wherein the bending portion is connected to the locking portion by being bent at a right angle after the bending portion is terminated so as to come into contact with the locking portion in the axial direction of the locking portion.

22. The clip according to claim 16, wherein a width of the bending portion increases toward the distal side.

23. The clip according to claim 22, wherein the arm is bent inward at a boundary between the linear portion linearly formed on the distal side from the bending portion and the bending portion, a recess which is further recessed in a width direction compared to other portions of the linear portion is formed on the proximal side of the linear portion, and in a state where the plurality of arms is closed, the clamping member is configured to be fitted to the recess.

24. An endoscopic treatment instrument, comprising:
the clip of claim 16;
the elongated sheath; and
the operation wire that is inserted into the elongated sheath such that the operation wire is movable forward and backward,
wherein the clip is mounted on the distal side of the operation wire.

* * * * *